United States Patent
King et al.

(10) Patent No.: US 11,155,624 B2
(45) Date of Patent: Oct. 26, 2021

(54) ANTIBODIES DIRECTED AGAINST PROGRAMMED DEATH-1 (PD-1)

(71) Applicants: ANAPTYSBIO, INC., San Diego, CA (US); TESARO, INC., Waltham, MA (US)

(72) Inventors: David J. King, Encinitas, CA (US); Marilyn Kehry, San Diego, CA (US); Baochuan Huang, Waltham, MA (US)

(73) Assignees: ANAPTYSBIO, INC., San Diego, CA (US); Tesaro, Inc., Waltham, MA (US)

( * ) Notice: Subject to any disclaimer, the term of this patent is extended or adjusted under 35 U.S.C. 154(b) by 216 days.

(21) Appl. No.: 16/346,485

(22) PCT Filed: Nov. 1, 2017

(86) PCT No.: PCT/US2017/059618
§ 371 (c)(1),
(2) Date: Apr. 30, 2019

(87) PCT Pub. No.: WO2018/085468
PCT Pub. Date: May 11, 2018

(65) Prior Publication Data
US 2019/0256600 A1 Aug. 22, 2019

Related U.S. Application Data

(60) Provisional application No. 62/416,128, filed on Nov. 1, 2016, provisional application No. 62/427,777, filed on Nov. 29, 2016.

(51) Int. Cl.
| | |
|---|---|
| *C07K 16/28* | (2006.01) |
| *A61K 39/395* | (2006.01) |
| *C12N 15/63* | (2006.01) |
| *A61K 45/06* | (2006.01) |
| *A61K 39/00* | (2006.01) |

(52) U.S. Cl.
CPC ...... *C07K 16/2818* (2013.01); *A61K 39/3955* (2013.01); *A61K 45/06* (2013.01); *C07K 16/2803* (2013.01); *C12N 15/63* (2013.01); *A61K 2039/505* (2013.01); *C07K 2317/33* (2013.01); *C07K 2317/41* (2013.01); *C07K 2317/524* (2013.01); *C07K 2317/53* (2013.01); *C07K 2317/56* (2013.01); *C07K 2317/76* (2013.01); *C07K 2317/92* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,122,464 A | 6/1992 | Wilson et al. |
| 5,464,758 A | 11/1995 | Gossen et al. |
| 5,770,359 A | 6/1998 | Wilson et al. |
| 5,814,618 A | 9/1998 | Bujard et al. |
| 7,029,674 B2 | 4/2006 | Carreno et al. |
| 7,101,550 B2 | 9/2006 | Wood et al. |
| 7,105,328 B2 | 9/2006 | Wood |
| 7,112,715 B2 | 9/2006 | Chambon et al. |
| 7,414,171 B2 | 8/2008 | Honjo |
| 7,488,802 B2 | 2/2009 | Collins et al. |
| 7,595,048 B2 | 9/2009 | Honjo et al. |
| 7,700,301 B2 | 4/2010 | Wood et al. |
| 7,709,214 B2 | 5/2010 | Freeman et al. |
| 8,008,449 B2 | 8/2011 | Korman et al. |
| 8,088,905 B2 | 1/2012 | Collins et al. |
| 8,168,757 B2 | 5/2012 | Finnefrock et al. |
| 8,216,996 B2 | 7/2012 | Minato |
| 8,460,886 B2 | 6/2013 | Shibayama |
| 8,563,314 B2 | 10/2013 | Gregory |
| 8,586,038 B2 | 11/2013 | Yang |
| 8,609,625 B2 | 12/2013 | Lan |
| 8,728,474 B2 | 5/2014 | Honjo et al. |
| 8,927,697 B2 | 1/2015 | Davis et al. |
| 8,993,731 B2 | 3/2015 | Tyson et al. |
| 9,102,728 B2 | 8/2015 | Tyson |
| 9,181,342 B2 | 11/2015 | Davis |
| 9,815,897 B2 | 11/2017 | King et al. |
| 10,738,117 B2 | 8/2020 | King et al. |
| 2002/0100068 A1 | 7/2002 | Chambon et al. |
| 2002/0164600 A1 | 11/2002 | Freeman |
| 2004/0213795 A1 | 10/2004 | Collins et al. |

(Continued)

FOREIGN PATENT DOCUMENTS

| | | |
|---|---|---|
| CA | 2932966 A1 | 6/2015 |
| EP | 2397155 | 12/2011 |

(Continued)

OTHER PUBLICATIONS

Goldsby, Immunology, 5th edition, 2003, pp. 82-84.*
Rudikoff, et al. (Proc. Natl. Acad. Sci. USA, 79(6); 1982; pp. 1979-1983.*
Brummell et al. (Biochemistry 32:1180-1187 (1993)).*
Kobayashi et al. (Protein Engineering 12:879-844 (1999)).*
Brorson et al. (J. Immunol. 163:6694-6701 (1999)).*
Coleman (Research in Immunol. 145:33-36 (1994)).*
Casset et al (Biochemical and Biophysical Research Communications, 307:198-205, 2003.*

(Continued)

*Primary Examiner* — Bridget E Bunner
*Assistant Examiner* — Fozia M Hamud
(74) *Attorney, Agent, or Firm* — Fish & Richardson P.C.

(57) ABSTRACT

The disclosure provides antibody agents that bind to a programmed death-1 (PD-1) protein. Particular immunoglobulin heavy chain polypeptide and immunoglobulin light chain polypeptide sequences are explicitly provided. Also provided are related nucleic acids, vectors, compositions, and methods of using the anti-PD-1 antibody agent to treat a disorder or disease that is responsive to PD-1 inhibition, such as cancer or an infectious disease.

14 Claims, 1 Drawing Sheet
Specification includes a Sequence Listing.

(56) References Cited

U.S. PATENT DOCUMENTS

| | | |
|---|---|---|
| 2004/0241745 A1 | 12/2004 | Honjo |
| 2007/0041982 A1 | 2/2007 | Ponath et al. |
| 2007/0092504 A1 | 4/2007 | Carreno |
| 2008/0311117 A1 | 12/2008 | Col lins |
| 2009/0028857 A1 | 1/2009 | Li |
| 2009/0060924 A1* | 3/2009 | Korytko ............... A61P 19/08 424/172.1 |
| 2009/0093024 A1 | 4/2009 | Bowers et al. |
| 2010/0028330 A1 | 2/2010 | Col lins et al. |
| 2010/0086550 A1 | 4/2010 | Kang |
| 2010/0151492 A1 | 6/2010 | Ah med |
| 2011/0008369 A1 | 1/2011 | Finnefrock et al. |
| 2011/0081341 A1 | 4/2011 | Honjo |
| 2011/0150892 A1 | 6/2011 | Th udium et al. |
| 2011/0171215 A1 | 7/2011 | Davis et al. |
| 2011/0171220 A1 | 7/2011 | Davis |
| 2011/0229461 A1 | 9/2011 | Tyson |
| 2011/0287485 A1 | 11/2011 | Bowers et al. |
| 2012/0039906 A1 | 2/2012 | Olive |
| 2012/0114649 A1 | 5/2012 | Langermann |
| 2012/0269806 A1 | 10/2012 | Sykes et al. |
| 2013/0035472 A1 | 2/2013 | Horlick et al. |
| 2013/0095098 A1 | 4/2013 | Tyson |
| 2013/0109843 A1 | 5/2013 | Carven |
| 2013/0133091 A1 | 5/2013 | Korman |
| 2013/0156774 A1 | 6/2013 | Kuchroo |
| 2013/0164294 A1 | 6/2013 | Honjo |
| 2013/0202623 A1 | 8/2013 | Chomont |
| 2013/0217656 A1 | 8/2013 | Tsokos |
| 2013/0291136 A1 | 10/2013 | Freeman |
| 2013/0309250 A1 | 11/2013 | Cogswell |
| 2013/0310266 A1 | 11/2013 | Liang |
| 2014/0004081 A1 | 1/2014 | Cobbold |
| 2014/0220021 A1 | 8/2014 | Shibayama et al. |
| 2015/0125955 A1 | 5/2015 | Chomont et al. |
| 2015/0152180 A1 | 6/2015 | Davis et al. |
| 2015/0203579 A1 | 7/2015 | Papadopoulos et al. |
| 2015/0210769 A1 | 7/2015 | Freeman et al. |
| 2015/0274844 A1 | 10/2015 | Blankenship et al. |
| 2015/0366174 A1 | 12/2015 | Burova et al. |
| 2016/0068586 A1 | 3/2016 | Tyson |
| 2016/0176962 A1 | 6/2016 | Murriel |
| 2016/0206754 A1 | 7/2016 | Chang |
| 2016/0208021 A1 | 7/2016 | Chang |
| 2019/0256600 A1 | 8/2019 | King |

FOREIGN PATENT DOCUMENTS

| | | |
|---|---|---|
| EP | 2638061 | 9/2013 |
| WO | WO 92/08796 | 5/1992 |
| WO | WO 94/28143 | 12/1994 |
| WO | WO 2001/014557 | 3/2001 |
| WO | WO 2002/078731 | 10/2002 |
| WO | WO 2003/042402 | 5/2003 |
| WO | WO 2004/056875 | 7/2004 |
| WO | WO 2008/083174 | 7/2008 |
| WO | WO 2008/084261 | 7/2008 |
| WO | WO 2008/156712 | 12/2008 |
| WO | WO 2009/026472 | 2/2009 |
| WO | WO 2009/087381 | 7/2009 |
| WO | WO 2010/029434 | 3/2010 |
| WO | WO 2010/029435 | 3/2010 |
| WO | WO 2011/090762 | 7/2011 |
| WO | WO 2011/100841 | 8/2011 |
| WO | WO 2011/110604 | 9/2011 |
| WO | WO 2011/110621 | 9/2011 |
| WO | WO 2012/017003 | 2/2012 |
| WO | WO 2012/135408 | 10/2012 |
| WO | WO 2013/022091 | 2/2013 |
| WO | WO 2013/128194 | 9/2013 |
| WO | WO 2013/169693 | 11/2013 |
| WO | WO 2013/174997 | 11/2013 |
| WO | WO 2013/177102 | 11/2013 |
| WO | WO 2013/181452 | 12/2013 |
| WO | WO 2014/179664 | 11/2014 |
| WO | WO 2015/112800 | 7/2015 |
| WO | WO 2015/112900 | 7/2015 |
| WO | WO 2015/138920 | 9/2015 |
| WO | WO 2015/145360 | 10/2015 |
| WO | WO 2015/196051 | 12/2015 |
| WO | WO 2016/020856 | 2/2016 |
| WO | WO 2016/054555 | 4/2016 |
| WO | WO 2016/100882 | 6/2016 |
| WO | WO 2016/100924 | 6/2016 |
| WO | WO 2016/106159 | 6/2016 |
| WO | WO 2016/109310 | 7/2016 |
| WO | WO 2016/112870 | 7/2016 |
| WO | WO 2016/126858 | 9/2016 |
| WO | WO 2016/161270 | 10/2016 |
| WO | WO 2017/019894 | 11/2017 |
| WO | WO 2018/005818 | 1/2018 |
| WO | WO 2018/129553 | 7/2018 |
| WO | WO 2018/129559 | 7/2018 |
| WO | WO 2019/067978 | 4/2019 |

OTHER PUBLICATIONS

Qin et al, Frontiers in Immunology, 2019; vol. 10, pp. 1-16.*

Mellati et al, Diabetes Care vol. 38, Sep. 2015.*

Anderson, 2016; https://doi.org/10.1016/j.immuni.2016.05.001.*

Acierto et al., "Biomarkers for Immunostimulatory Monoclonal Antibodies in Combination Strategies for Melanoma and other Tumor Types," Clinical Cancer Research, 19(5): 1009-1020 (Mar. 1, 2013).

Agrawal et al: "Nivolumab Dose Selection: Challenges, Opportunities, and Lessons Learned for Cancer Immunotherapy", Journal for Immunotherapy of Cancer, 2016, 4:1-11.

Al Magro et al., "Humanization of antibodies," Frontiers in Bioscience; 13: 1619-1633 (2008).

Altschu L et al., "Gapped BLAST and PSI-BLAST: a new generation of protein database search programs," Nucleic Acids Research, 25(17): 3389-3402 (1997).

Altschul et al., "Basic local alignment search tool," J. Molecular Biol, 1990, 215(3):403-410.

An, Therapeutic Monoclonal Antibodies From Bench to Clinic (An ed. ) 3-75 (John Wiley & Sons, Inc., Hoboken, NJ 2009).

Aspeslagh et al., "Rationale for anti-OX40 cancer immunotherapy," European Journal of Cancer, 52: 50-66 (2016).

Ayers et al., "IFN-γ-related mRNA profile predicts clinical response to PD-1 blockade," J. Clin. Invest., 2017, 127(8):2930-2940.

Barber et al., "Restoring function in exhausted CDS T cells during chronic viral infection," Nature, 439: 682-687 (Feb. 9, 2006).

Bennett et al., "Program death-1 engagement upon TCR activation has distinct effects on costimulation and cytokine-driven proliferation: attenuation of ICOS, IL-4, and IL-21, but not CD28, IL-7, and IL-15 responses," J Immunol., 2003, 170:711-8.

Bertsias et al., "Genetic, Immunologic, and Immunohistochemical Analysis of the Programmed Death 1/Progmmmed Death Ligand 1 Pathway in Human Systemic Lupus Erythematosus," Arthritis & Rheumatism, 60(1): 207-218 (Jan. 2009).

Bhatia et al., "Immunobiology of Merkel cell carcinoma: implications for immunotherapy of a polyomavirus-associated cancer," Curr. Oncol. Rep., 13(6): 488-497 (Dec. 2011).

Biegert et al., "Sequence context-specific profiles for homology searching," PNAS, 106(10): 3770-3775 (Mar. 10, 2009).

Bird et al., "Single-Chain Antigen-Binding Proteins," Science, 242: 423-426 (Oct. 21, 1988).

Blank et al., "PD-L 1/B7H-1 Inhibits the Effector Phase of Tumor Rejection by T Cell Receptor (TCR) Transgenic cos+ T Cells," Cancer Research, 64: 1140-1145 (Feb. 1, 2004).

Bohnsack et al., "Adaption of the immune-related response criteria: irRecist," ESMO, 2014, Abstract 4958.

Bowers et al., "Coupling mammalian cell surface display with somatic hypermutation for the discovery and maturation of human antibodies," PNAS, 108(51 ): 20455-20460 (Dec. 20, 2011).

Brash et al., "Strontium Phosphate Transfection of Human Cells in Primary Culture: Stable Expression of the Simian Virus 40 Large-T-Antigen Gene in Primary Human Bronchial Epithelial Cells," Molecular and Cellular Biology, 7(5): 2031-2034 (May 1987).

(56) References Cited

OTHER PUBLICATIONS

Brown et al., "Blockade of Programmed Death-1 Ligands on Dendritic Cells Enhances T Cell Activation and Cytokine Production," The Journal of Immunology, 170: 1257-1266 (2003).
Brown et al., Tolerance of single, but not multiple, amino acid replacements in antibody VH CDR 2: a means of minimizing B cell wastage from somatic hypermutation? The Journal of Immunology, i 56.9 (1996): 3285-3291.
Colberre-Garapin et al., "A new dominant hybrid selective marker for higher eukaryotic cells," J Mol. Biol., 1981, 150:1-14.
Conese et al., "Gene Therapy Progress and Prospects: Episomally maintained self-replicating systems," Gene Therapy, 11: 1735-1741 (2004).
David et al., "Protein iodination with solid state lactoperoxidase," Biochemistry, 1974, 13:1014-1021.
Davies et al., "Antibody-antigen complexes," Annual Rev Biochem, 1990, 59:439-473.
De Genst et al., "Antibody repertoire development in camelids," Developmental & Comparative Immunology, 30:187-198 (2006).
De St. Groth et al., "Production of Monoclonal Antibodies: Strategy and Tactics," Journal of Immunological Methods, 35: 1-21 (1980).
Dong et al., "Tumor-associated B7-H1 promotes T-cell apoptosis: A potential mechanism of immune evasion," Nature Medicine, 8(8): 793-800 (Aug. 2002).
Durbin et al., Biological Sequence Analysis, Probabilistic Models of Proteins and Nucleic Acids, (Durbin et al., ed.) 1-356 (Cambridge University Press, Cambridge, UK 1998).
Eisenhauer, et al., "New response evaluation criteria in solid tumors: Revised RECIST guideline (version 1. 1.)," Eur. J. of Cancer, 2009, 45:228-247.
Extended Search Report issued by the European Patent Office for Application No. 14 791454.3 dated Feb. 28, 2017.
Flies et al., "Blockade of the B7-H1/PD-1 Pathway for Cancer Immunotherapy," Yale Journal of Biology and Medicine, 84: 409-421 (2011).
Freeman et al., "Engagement of the PD-1 Immunoinhibitory Receptor by a Novel 87 Family Member Leads to Negative Regulation of Lymphocyte Activation," J. Exp. Med. 192(7): 1027-1034 (Oct. 2, 2000).
Fuhrmann-Benzakein et al., "Inducible and irreversible control of gene expression using a single transgene," Nucleic Acids Research, 28(23): 1-5 (2000).
Greenwald et al., "The 87 Family Revisited," Annu. Rev. Immunol., 23: 515-548 (2005).
Hamanishi et al., "Programmed cell death 1 ligand 1 and tumor-infiltrating CDS+ T lymphocytes are prognostic factors of human ovarian cancer," PNAS, 104(9): 3360-3365 (Feb. 27, 2007).
Hirano et al., "Blockade of B7-H1 and PD-1 by Monoclonal Antibodies Potentiates Cancer Therapeutic Immunity," Cancer Research, 65(3): 1089-1096 (Feb. 1, 2005).
Holliger et al., "Engineered antibody fragments and the rise of single domains," Nature Biotechnology, 23(9): 1126-1136 (Sep. 2005).
Hotzel et al., "A strategy for risk mitigation of antibodies with fast clearance," mAbs, 4(6): 753-760 (Nov./Dec. 2012).
Hou et al., "Humanization of an Anti-CD34 Monoclonal Antibody by Complementarity-determining Region Grafting Based on Computer-assisted Molecular Modelling," J. Biochem., 144: 115-120 (2008).
Hunter et al., "Preparation of iodine-131 labelled human growth hormone of high specific activity," Nature, 1962, 194:495-496.
Huston et al., "Protein engineering of antibody binding sites: Recovery of specific activity in an anti-digoxin single-chain Fv analogue produced in *Escherichia coli*," PNAS USA, 85: 5879-5883 (Aug. 1988).
Indra et al., "Temporally-controlled site-specific mutagenesis in the basal layer of the epidermis: comparison of the recombinase activity of the tamoxifen-inducible Cre-ERT and Cre-ERT2 recombinases," Nucleic Acids Research, 27(22): 4324-4327 (1999 ).

International Bureau of WIPO, International Preliminary Report on Patentability in International Patent Application No. PCT/US2014/036525 (dated Nov. 12, 2015).
International Search Report for PCT/US2018/013029, 8 pages (dated Jun. 6, 2018).
Ishida et al., "Induced expression of PD-1, a novel member of the immunoglobulin gene superfamily, upon programmed cell death," The EMBO Journal, 11(11): 3887-3895 (1992).
Iwai et al., "Involvement of PD-L 1 on tumor cells in the escape from host immune system and tumor immunotherapy by PD-L 1 blockade," PNAS, 99(19): 12293-12297 (Sep. 17, 2002).
Iwai et al., "PD-1 blockade inhibits hematogenous spread of poorly immunogenic tumor cells by enhanced recruitment of effector T cells," International Immunology, 17(2): 133-144 (2004).
Jack et al., "Looping out and deletion mechanism for the immunoglobulin heavy-chain class switch," PNAS USA, 85: 1581-1585 (Mar. 1988).
Johnston, "Biolistic transformation: microbes to mice," Nature, 1990, 346:776-777.
Kasagi et al., "Anti-Programmed Cell Death 1 Antibody Reduces co4+po-1+ T Cells and Relieves the Lupus-Like Nephritis of NZB/W F1 Mice," The Journal of Immunology, 184: 2337-2347 (Feb. 5, 2010).
Kashmiri et al., "SOR grafting—a new approach to antibody humanization," Methods, 36: 25-34 (2005).
Kearney et al., "A New Mouse Myeloma Cell Line That Has Lost Immunoglobulin Expression But Permits the Construction of Antibody-Secreting Hybrid Cell Lines," The Journal of Immunology, 123(4): 1548-1550 (Oct. 1979).
Kent et al., "Ouabain Resistance Conferred by Expression of the cDNA for a Murine Na+,K+-ATPase a Subunit," Science, 237: 901-903 (Aug. 21, 1987).
Kitts et al., "A method for producing recombinant baculovirus expression vectors at high frequency," Biotechniques, 1993, 14:810-817.
Kohler and Milstein, "Derivation of specific antibody-producing tissue culture and tumor lines by cell fusion," Eur. J. Immunol., 1976, 5:511-519.
Kramer & Fussenegger, "Transgene control engineering in mammalian cells," Methods Mol. Biol, 2005, 308:123-144.
Kroner et al., "A PD-1 Polymorphism Is Associated with Disease Progression in Multiple Sclerosis," Annals of Neurology, 58(1): 50-57 (Jul. 2005).
Latchman et al., "PD-L2 is a second ligand for PD-1 and inhibits T cell activation," Nature Immunology, 2(3): 261-268 (Mar. 2001).
Le et al., "PD-1 Blockade in Tumors with Mismatch-Repair Deficiency," N Engl. J Med, 2015, 372(26):2509-2520.
Lonberg, "Human antibodies from transgenic animals," Nature Biotechnology, 23(9): 1117-1125 (Sep. 2005).
Lonberg, "Human Monoclonal Antibodies from Transgenic Mice," Therapeutic Antibodies. Handbook of Experimental Pharmacology 181, (Chernajovsky et al., eds.), 69-97 (Springer-Verlag, Berlin 2008).
Lowy et al., "Isolation of Transforming DNA: Cloning the Hamster aprt Gene," Cell, 22: 817-823 (Dec. 1980).
Lucklow et al, "Efficient generation of infectious recombinant baculoviruses by site-specific transposon-mediated insertion of foreign genes into a baculovirus genome propagated in *Escherichia coli*," J. Virol., 1993, 67:4566-4579.
Lucklow, "Baculovirus systems for the expression of human gene products," Curr. Opin. Biotechnol.,1993, 4:564-572.
Luckow et al., "Efficient Generation of Infectious Recombinant Baculoviruses by Site-Specific Transposon-Mediated Insertion of Foreign Genes into a Baculovirus Genome Propagated in *Escherichia coli*," Journal of Virology, 67(8): 4566-4579 (Aug. 1993).
Mahoney et al., "The Next Immune-Checkpoint Inhibitors: PD-1/PD-L 1 Blockade in Melanoma," Clinical Therapeutics, 37(4):764-782 (2015).
Malmqvist, "Biospecific interaction analysis using biosensor technology," Nature, 1993, 361:186-87.
McConnell et al., "An integrated approach to extreme thermostabilization and affinity maturation of an antibody," Protein Engineering, Design & Selection, 26(2): 151-163 (2013).

(56) References Cited

OTHER PUBLICATIONS

Mulligan et al., "Selection for animal cells that express the *Escherichia coli* gene coding for xanthine-guanine phosphoribosyltransferase," PNAS USA, 78(4): 2072-2076 (Apr. 1981).
Myers and Miller, "Optimal alignments in linear space," CABIOS, 1989, 4:11-17.
Ngiow et al., "Anti-TIM3 Antibody Promotes T Cell IFN-γ-Mediated Antitumor Immunity and Suppresses Established Tumors," Cancer Res., 71(10): 3540-3551 (May 15, 2011).
Ni et al., "PD-1 gene haplotype is associated with the development of type 1 diabetes mellitus in Japanese children," Hum. Genet., 121: 223-232 (2007).
Nielsen et al., "Association of a putative regulatory polymorphism in the PD-1 gene with susceptibility to type 1 diabetes," Tissue Antigens, 62: 492-497 (2003).
Nishimura et al., "Development of Lupus-like Autoimmune Diseases by Disruption of the PD-1 Gene Encoding an ITIM Motif-Carrying Immunoreceptor," Immunity, 11: 141-151 (Aug. 1999).
Nishina et al., "Developing a common language for tumor response to immunotherapy: immune-related response criteria using unidimensional measurements," Clin. Cancer Res., 2013, 19(14):3936-43.
No et al., "Ecdysone-inducible gene expression in mammalian cells and transgenic mice," PNAS USA, 93: 3346-3351 (Apr. 1996).
Nygren, "Conjugation of Horseradish Peroxidase to Fab Fragments with Different Homobifunctional and Heterobifunctional Cross-Linking Reagents," The Journal of Histochemistry and Cytochemistry, 30(5): 407-412 (1982).
O'Hare et al., "Transformation of mouse fibroblasts to methotrexate resistance by a recombinant plasmid expressing a prokaryotic dihydrofolate reductase," PNAS USA, 78(3): 1527-1531 (Mar. 1981).
Okazaki et al., "PD-1 and PD-1 ligands: from discovery to clinical application," Int. Immunol., 2007, 19(7):813-824.
Osbourn et al., "Directed selection of MIP-1 a neutralizing CCR5 antibodies from a phage display human antibody library," Nature Biotechnology, 16: 778-781 (Aug. 1998).
Pain et al, "Preparation of protein A-peroxidase monoconjugate using a heterobifunctional reagent, and its use in enzyme immunoassays," J. Immunol. Meth., 1981, 40: 219-230.
Parry et al., "CTLA-4 and PD-1 Receptors Inhibit T-Cell Activation by Distinct Mechanisms," Molecular and Cellular Biology, 25(21): 9543-9553 (Nov. 2005).
Patnaik et al., "Phase I study of MK-3475 (anti-PD-1 monoclonal antibody) in patients with advanced solid tumors," J. Clin. Oncol., 30(Abstract No. 2512): 30 (2012 ).
Porichis et al., "Role of PD-1 in HIV Pathogenesis and as Target for Therapy," Curr. HIV/AIDS Rep., 9(1): 81-90 (Mar. 2012).
Rituparna Das et al: "Combination Therapy With Anti-CTLA-4 and Anti-PD-I Leads to Distinct Immunologic Changes in Vivo", The Journal of Immunology, 2014, 194(3):950-959.
Robert et al: "Anti-Programmed-Death-Receptor-I Treatment With Pembrolizumab in Ipilimumab-Refractory Advanced Melanoma: A Randomized Dose-Comparison Cohort of a Phase 1 Trial", The Lancet, 2014, 384(9948):1109-1117.
Sakuishi et al., "Targeting Tim-3 and PD-1 pathways to reverse T cell exhaustion and restore anti-tumor immunity," The Journal of Experimental Medicine, 207(10): 2187-2194 (Sep. 27, 2010).
Sanmam Ed et al., "Agonists of Co-stimulation in Cancer Immunotherapy Directed Against CD137, OX40, GITR, CD27, CD28, and ICOS," Seminars in Oncology 42(4): 640-655 (Aug. 2015).
Santerre et al., "Expression of prokaryotic genes for hygromycin B and G418 resistance as dominant-selection markers in mouse L cells," Gene, 1984, 30:147-156.
Search Report issued by the European Patent Office dated Oct. 28, 2016.
Sharpe et al., "The function of programmed cell death 1 and its ligands in regulating autoimmunity and infection," Nature Immunology, 8(3): 239-245 (Mar. 2007).
Silva et al., "The S228P mutation prevents in vivo and in vitro IgG4 Fab-arm exchange as demonstrated using a combination of novel quantitative immunoassays and physiological matrix preparation," J. Biol. Chem., 2015, 290(9):5462-5469.
Soding, "Protein homology detection by HMM-HMM comparison," Bioinformatics, 21(7): 951-960 (2005).
Szybalska et al., "Genetics of Human Cell Lines, IV. DNA-Mediated Heritable Transformation of a Biochemical Trait," PNAS., 48: 2026-2034 (1962).
Tahoori et al., "Association of programmed cell death-1 (PDCD-1) gene polymorphisms with rheumatoid arthritis in Iranian patients," Clinical and Experimental Rheumatology, 29: 763-767 (Sep. 2011).
Tang et al., "Programmed Death 1 Pathway inhibition in Metastatic Renal Cell Cancer and Prostate Cancer," Curr. Oncol., Rep., 15: 98-104 (2013).
Topalian et al., "Safety, Activity, and Immune Correlates of Anti-PD-1 Antibody in Cancer," The New England Journal of Medicine, 366(26): 2443-2454 (Jun. 28, 2012).
Turnis et al., "Combinatorial immunotherapy: PD-1 may not be LAG-ing behind anymore." Oncoimmunology, 1.7 (2012): 1172-1174.
United States Patent and Trademark Office, International Search Report in International Patent Application No. PCT/US2014/036525 (dated Dec. 24, 2014).
Urlaub et al., "Isolation of Chinese hamster cell mutants deficient in dihydrofolate reductase activity," PNAS USA, 77(7): 4216-4220 (Jul. 1980).
Vitetta et al., "Considering Therapeutic Antibodies," Science, 313: 308-309 (Jul. 21, 2006).
Weber, "Immune Checkpoint Proteins: A New Therapeutic Paradigm for Cancer—Preclinical Background: CTLA-4 and PD-1 Blockade," Seminars in Oncology, 37(5): 430-439 (Oct. 2010).
Westdorp et al., "Opportunities for immunotherapy in microsatellite instable colorectal cancer," Cancer Immunol. Immunother., 2016, 65(10):1249-1259.
Wigler et al., "Transfer of Purified Herpes Virus Thymidine Kinase Gene to Cultured Mouse Cells," Cell, 11: 223-232 (May 1977).
Wigler et al., "Transformation of mammalian cells with an amplifiable dominant-acting gene," PNAS USA, 77(6): 3567-3570 (Jun. 1980).
Woo et al., "Immune inhibitory molecules LAG-3 and PD-1 synergistically regulate T cell function to promote tumoral immune escape," Cancer Res., 72(4): 917-927 (Feb. 15, 2012).
Yamazaki et al., "Expression of Programmed Death 1 Ligands by Murine T Cells and APC," The Journal of Immunology, 169: 5538-5545 (2002).
Clinicaltrials.gov [online] "ClinicalTrials.gov NCT02657889: Niraparib in Combination With Pembrolizumab in Patients With Triple-negative Breast Cancer or Ovarian Cancer," Aug. 2, 2016, retrieved Jun. 12, 2020, retrieved from URL>https://clinicaltrials.gov/ct2/show/NCT02657889?term=NCT02657889&draw=2&rank=1.
Clinicaltrials.gov [online] "ClinicalTrials.gov NCT02861573: Study of Pembrolizumab (MK-3475) Combination Therapies in Metastatic Castration-Resistant Prostate Cancer (MK-3475-365/KEYNOTE-365)," Oct. 14, 2016, retrieved on Apr. 1, 2020, retrieved from URL>https://clinicaltrials.gov/ct2/history/NCT02861573?A=2&B=2&C=merged#StudyPageTop.
Clinicaltrials.gov [online] "Niraparib in Combination With Pembrolizumab in Patients With Triple-negative Breast Cancer or Ovarian Cancer (TOPACIO)," Mar. 1, 2017, retrieved Apr. 1, 2020, retrieved from URL>https://clinicaltrials.gov/ct2/show/NCT02657889?term=TESARO&draw=2&rank=5.
EP Search Report in European Appln. No. 20150603.7, dated May 14, 2020, 15 pages.
EP Search Report in European Appln. No. 17867513.8, dated Apr. 8, 2020, 4 pages.
Friedlander: "A phase 1b study of the anti-PD-1 monoclonal antibody BGB-A317 (A317) in combination with the PARP inhibitor BGB-290 (290) in advanced solid tumors," Journal of Clinical Oncology, 2017, 35(15 suppl): 5 pages.
Laken et al., "Identification and characterization of TSR-042, a novel anti-human PD-1 therapeutic antibody," European Journal of Cancer, 2016, 69(1):S102.

(56) References Cited

OTHER PUBLICATIONS

Li et al., "A Mini-Review for Cancer Immunotherapy: Molecular Understanding of PD-1 /PD-L 1 Pathway & Translational Blockade of Immune Checkpoints," Int. J. Mol. Sci. 2016, 17(7):1151.
CAS Entry 2022215-59-2, STN, Oct. 31, 2016, 2 pages.

* cited by examiner

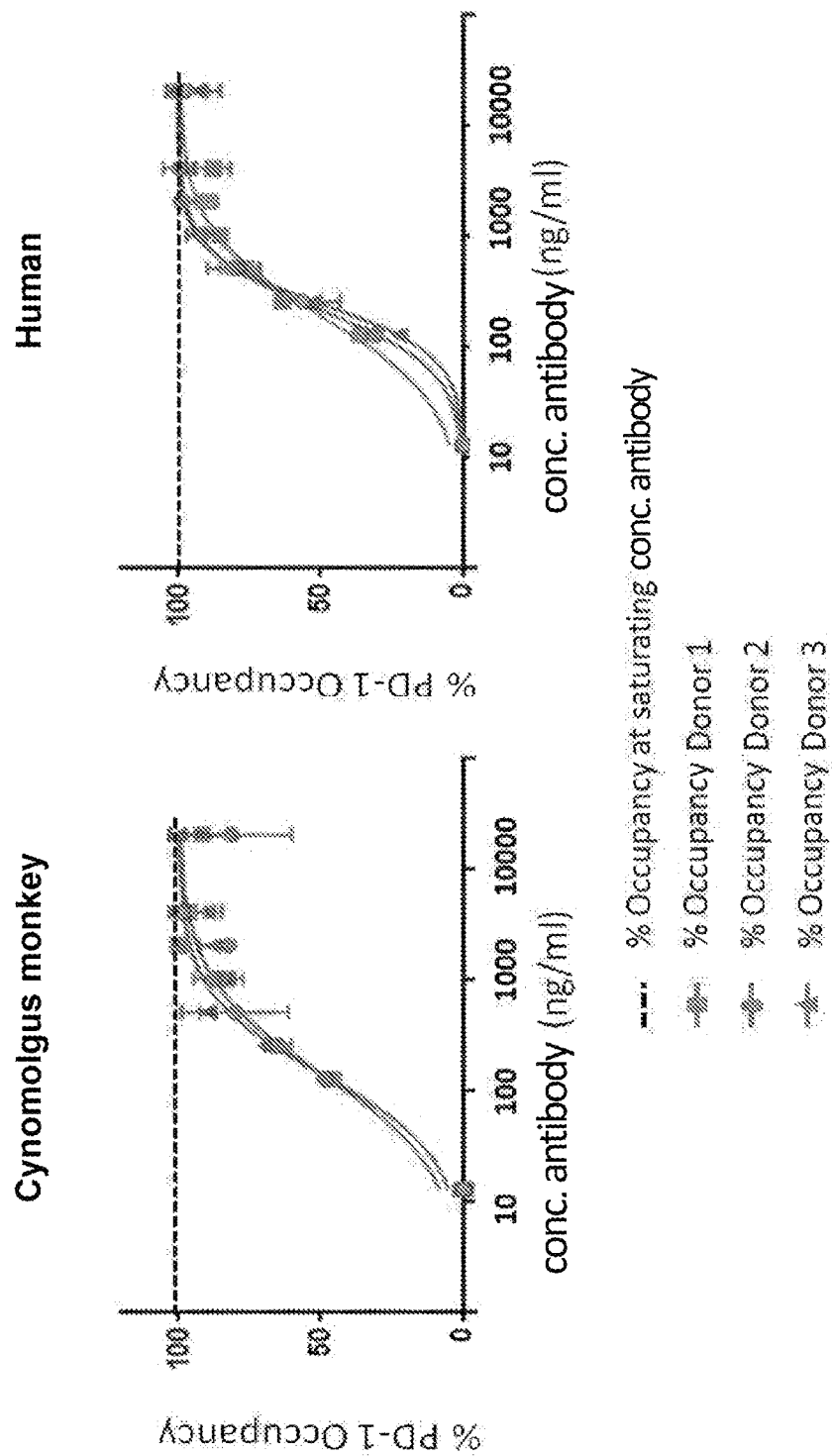

ANTIBODIES DIRECTED AGAINST PROGRAMMED DEATH-1 (PD-1)

CROSS-REFERENCE TO RELATED APPLICATIONS

This application is a 35 U.S.C. § 371 National Stage Application of International Application No. PCT/US17/59618, filed Nov. 1, 2017, which claims the benefit of U.S. Provisional Application Ser. No. 62/416,128 filed Nov. 1, 2016, and 62/427,777 filed Nov. 29, 2016, the contents of both of which are hereby incorporated by reference in their entirety.

INCORPORATION-BY-REFERENCE OF SEQUENCE LISTING

The contents of the file named "TSR-013US_ST25.txt", which was created on Apr. 24, 2019 and is 21 KB in size, are hereby incorporated by reference in their entirety.

BACKGROUND

Cancer is a serious public health problem, with about 595,690 people in the United States of America expected to die of cancer in 2016 alone according to the American Cancer Society, Cancer Facts & Figures 2016 (http://www.cancer.org/acs/groups/content/@research/documents/document/acspc-047079.pdf).

BRIEF SUMMARY OF THE INVENTION

Programmed Death 1 (PD-1) (also known as Programmed Cell Death 1) is a type I transmembrane protein of 268 amino acids originally identified by subtractive hybridization of a mouse T cell line undergoing apoptosis (Ishida et al., *Embo J* 11: 3887-95 (1992)). PD-1 is a member of the CD28/CTLA-4 family of T-cell regulators, and is expressed on activated T-cells, B-cells, and myeloid lineage cells (Greenwald et al., *Annu. Rev. Immunol.*, 23: 515-548 (2005); and Sharpe et al., *Nat. Immunol.*, 8: 239-245 (2007)).

Two ligands for PD-1 have been identified, PD ligand 1 (PD-L1) and PD ligand 2 (PD-L2), both of which belong to the B7 protein superfamily (Greenwald et al, supra). PD-L1 is expressed in a variety of cell types, including cells of the lung, heart, thymus, spleen, and kidney (see, e.g., Freeman et al., *J. Exp. Med.*, 192(7): 1027-1034 (2000); and Yamazaki et al., *J. Immunol.*, 169(10): 5538-5545 (2002)). PD-L1 expression is upregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine tumor cell lines (see, e.g., Iwai et al., *Proc. Nat.l Acad. Sci. USA*, 99(9): 12293-12297 (2002); and Blank et al., *Cancer Res.*, 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat. Immunol.*, 2(3): 261-238 (2001)). High PD-L1 expression in tumors, whether on the tumor cell, stroma, or other cells within the tumor microenvironment, correlates with poor clinical prognosis, presumably by inhibiting effector T cells and upregulating regulatory T cells (Treg) in the tumor.

PD-1 negatively regulates T-cell activation, and this inhibitory function is linked to an immunoreceptor tyrosine-based switch motif (ITSM) in the cytoplasmic domain (see, e.g., Greenwald et al., supra; and Parry et al., *Mol. Cell. Biol.*, 25: 9543-9553 (2005)). PD-1 deficiency can lead to autoimmunity. For example, C57BL/6 PD-1 knockout mice have been shown to develop a lupus-like syndrome (see, e.g., Nishimura et al., *Immunity*, 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens*, 62(6): 492-497 (2003); Bertsias et al., *Arthritis Rheum.*, 60(1): 207-218 (2009); Ni et al, *Hum. Genet.*, 121(2): 223-232 (2007); Tahoori et al., *Clin. Exp. Rheumatol.*, 29(5): 763-767 (2011); and Kroner et al., *Ann. Neurol.*, 58(1): 50-57 (2005)). Abnormal PD-1 expression also has been implicated in T-cell dysfunctions in several pathologies, such as tumor immune evasion and chronic viral infections (see, e.g., Barber et al., *Nature*, 439: 682-687 (2006); and Sharpe et al., supra).

Recent studies demonstrate that T-cell suppression induced by PD-1 also plays a role in the suppression of anti-tumor immunity. For example, PD-L1 is expressed on a variety of human and mouse tumors, and binding of PD-1 to PD-L1 on tumors results in T-cell suppression and tumor immune evasion and protection (Dong et al., *Nat. Med.*, 8: 793-800 (2002)). Expression of PD-L1 by tumor cells has been directly associated with their resistance to lysis by anti-tumor T-cells in vitro (Dong et al., supra; and Blank et al., *Cancer Res.*, 64: 1140-1145 (2004)). PD-1 knockout mice are resistant to tumor challenge (Iwai et al., *Int. Immunol.*, 17: 133-144 (2005)), and T-cells from PD-1 knockout mice are highly effective in tumor rejection when adoptively transferred to tumor-bearing mice (Blank et al., supra). Blocking PD-1 inhibitory signals using a monoclonal antibody can potentiate host anti-tumor immunity in mice (Iwai et al., supra; and Hirano et al., *Cancer Res.*, 65: 1089-1096 (2005)), and high levels of PD-L1 expression in tumors are associated with poor prognosis for many human cancer types (Hamanishi et al., *Proc. Natl. Acad. Sci. USA*, 104: 3360-335 (2007), Brown et al, *J. Immunol.*, 170: 1257-1266 (2003); and Flies et al., *Yale Journal of Biology and Medicine*, 84(4): 409-421 (2011)).

In view of the foregoing, strategies for inhibiting PD-1 activity to treat various types of cancer and for immunopotentiation (e.g., to treat infectious diseases) have been developed (see, e.g., Ascierto et al., *Clin. Cancer Res.*, 19(5): 1009-1020 (2013)). In this respect, monoclonal antibodies targeting PD-1 have been developed for the treatment of cancer (see, e.g., Weber, *Semin. Oncol.*, 37(5): 430-4309 (2010); and Tang et al., *Current Oncology* Reports, 15(2): 98-104 (2013)). For example, nivolumab (also known as BMS-936558) produced complete or partial responses in non-small-cell lung cancer, melanoma, and renal-cell cancer in a Phase I clinical trial (see, e.g., Topalian, *New England J. Med.*, 366: 2443-2454 (2012)), and is currently in Phase III clinical trials. MK-3575 is a humanized monoclonal antibody directed against PD-1 that has shown evidence of antitumor activity in Phase I clinical trials (see, e.g., Patnaik et al., 2012 *American Society of Clinical Oncology (ASCO) Annual Meeting*, Abstract #2512). In addition, recent evidence suggests that therapies which target PD-1 may enhance immune responses against pathogens, such as HIV (see, e.g., Porichis et al., *Curr. HIV/AIDS Rep.*, 9(1): 81-90 (2012)). Despite these advances, however, the efficacy of these potential therapies in humans may be limited.

There is a need for additional antagonists of PD-1 (e.g., an antibody) that bind PD-1 with high affinity and effectively neutralize PD-1 activity.

The present disclosure provides antibody agents and various compositions and methods relating thereto including, for example, polypeptides, nucleic acids, cells, and various methodologies, etc.

The present invention provides novel antibodies that bind to PD-1. In some embodiments, antibodies of the present invention bind to PD-1 with high affinity and effectively neutralize PD-1 activity. In some embodiments, antibody heavy chain polypeptide (SEQ ID NO:1) and light chain polypeptide (SEQ ID NO:2) sequences are explicitly provided.

The present disclosure provides a polypeptide or an isolated immunoglobulin heavy chain polypeptide having an amino acid sequence as set forth in SEQ ID NO:1. The present disclosure further provides a polypeptide or an isolated immunoglobulin heavy chain polypeptide having an amino acid sequence that shares at least about 90%, 91%, 92%, 93%, 94%, 95%, 96%, 97%, 98% or 99% overall identity with that set forth in SEQ ID NO:1. In some embodiments, sequence differences relative to the sequence set forth in SEQ ID NO:1 are not within the CDRs. In some embodiments, a polypeptide or an isolated immunoglobulin heavy chain polypeptide includes all three CDRs of SEQ ID NO:1. In some embodiments, a polypeptide or an immunoglobulin heavy chain polypeptide includes a signal peptide. In some embodiments, a polypeptide or an immunoglobulin heavy chain polypeptide which includes a signal peptide has an amino acid sequence as set forth in SEQ ID NO:5.

In some embodiments, a provided polypeptide or immunoglobulin heavy chain polypeptide is or comprises an IgG4 polypeptide. In some embodiments, a provided polypeptide or immunoglobulin heavy chain polypeptide comprises a human IGHG4*01 polypeptide. In some embodiments, a provided polypeptide or immunoglobulin heavy chain polypeptide comprises one or more mutations within the IgG heavy chain region. In some embodiments, a provided polypeptide or immunoglobulin heavy chain polypeptide comprises an IgG4 heavy chain constant region having one or more mutations in the heavy chain constant region. In some embodiments, a provided polypeptide or immunoglobulin heavy chain polypeptide comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include a serine to proline stabilizing mutation that prevents half molecule exchange with other IgG4 molecules. In some embodiments, the one or more mutations in hinge region of IgG4 may include an S228P mutation. See, e.g., J. Biol. Chem. 2015; 290(9):5462-5469.

The present disclosure provides a polypeptide or an isolated immunoglobulin light chain polypeptide having an amino acid sequence as set forth in SEQ ID NO:2. The present disclosure further provides a polypeptide or an isolated immunoglobulin light chain polypeptide having an amino acid sequence that shares at least about 90%, 91%, 92%, 93%, 94%, 95%, 96%, 97%, 98% or 99% overall identity with that set forth in SEQ ID NO:2. In some embodiments, sequence differences relative to the sequence set forth in SEQ ID NO:2 are not within the CDRs. In some embodiments, a polypeptide or an isolated immunoglobulin light chain polypeptide includes all three CDRs of SEQ ID NO:2. In some embodiments, a provided polypeptide or immunoglobulin light chain polypeptide is a kappa light chain. In some embodiments, a provided polypeptide or immunoglobulin light chain polypeptide comprises a human IGKC*01 polypeptide. In some embodiments, a polypeptide or an immunoglobulin light chain polypeptide includes a signal peptide. In some embodiments, a polypeptide or an immunoglobulin light chain polypeptide includes a signal peptide has an amino acid sequence as set forth in SEQ ID NO:6.

In some embodiments, the present disclosure provides an anti-PD-1 antibody agent comprising at least one immunoglobulin heavy chain having an amino acid sequence as set forth in SEQ ID NO:1 and at least one immunoglobulin light chain having an amino acid sequence as set forth in SEQ ID NO:2. In some embodiments an anti-PD-1 antibody agent comprises two immunoglobulin heavy chains, each having an amino acid sequence as set forth in SEQ ID NO:1. Alternatively or additionally, in some embodiments an anti-PD-1 antibody agent comprises two immunoglobulin light chains, each having an amino acid sequence as set forth in SEQ ID NO:2. In some embodiments, an anti-PD-1 antibody agent has a canonical antibody format.

In some embodiments, a provided heavy chain, light chain and/or antibody agent is glycosylated at one or more sites. In some embodiments, a glycan is N-linked to an Fc region. In some embodiments, an antibody agent is glycosylated at Asn297 (Kabat numbering).

In some embodiments, present disclosure provides a composition comprising one or more glycoforms of a heavy chain, light chain, and/or antibody agent as described herein. In some embodiments, a provided composition comprises plurality of glycoforms, present in specified absolute and/or relative amounts. In some embodiments, the present disclosure provides compositions that may be substantially free of one or more particular glycoforms of a heavy chain, light chain, and/or antibody agent as described herein.

In some embodiments, a provided heavy chain, light chain and/or antibody agent has a structure that includes one or more disulfide bonds. In some embodiments, the one or more disulfide bonds are or include a disulfide bond at the expected position for an IgG4 immunoglobulin.

In some embodiments, an anti-PD-1 antibody agent is administered with another antibody agent, such as one specific for lymphocyte-activation gene 3 (LAG-3) or T-cell immunoglobulin domain and mucin domain 3 protein (TIM-3).

In some embodiments, an antibody agent binds to PD-1 and another antigen, resulting in a "dual reactive" antibody agent (e.g., a bispecific antibody). For example, an antibody agent can bind to PD-1 and to another negative regulator of the immune system such as, for example, lymphocyte-activation gene 3 (LAG-3) or T-cell immunoglobulin domain and mucin domain 3 protein (TIM-3).

In addition, the present disclosure provides isolated or purified nucleic acid sequences encoding the foregoing immunoglobulin polypeptides, vectors comprising such nucleic acid sequences, isolated anti-PD-1 antibody agents comprising the foregoing immunoglobulin polypeptides, nucleic acid sequences encoding such anti-PD-1 antibody agents, vectors comprising such nucleic acid sequences, isolated cells comprising such vectors, compositions comprising such anti-PD-1 antibody agents or such vectors with a pharmaceutically acceptable carrier, and methods of treating cancer or infectious diseases in mammals by administering effective amounts of such compositions to mammals.

BRIEF DESCRIPTION OF THE DRAWING

The Drawing included herein, which is composed of the following Figures, is for illustration purposes only not for limitation.

FIG. 1 shows a graph depicting receptor occupancy of an exemplary anti-PD-1 antibody agent in human and cynomolgus monkey PBMCs.

DETAILED DESCRIPTION OF CERTAIN EMBODIMENTS

The present disclosure describes, at least in part, antibody agents and various compositions and methods relating thereto including, for example, polypeptides, nucleic acids, cells, and various methodologies, etc. In some embodiments, antigen-binding proteins of the present invention bind to PD-1 with high affinity and effectively neutralize PD-1 activity. In some embodiments, immunoglobulin heavy chain polypeptide (SEQ ID NO:1 and 5) and immunoglobulin light chain polypeptide (SEQ ID NO:2 and 6) sequence are explicitly provided. In some embodiments, an immunoglobulin heavy chain polypeptide and/or an immunoglobulin light chain polypeptide is isolated. The term "immunoglobulin" or "antibody," as used herein, refers to a protein that is found in blood or other bodily fluids of vertebrates, which is used by the immune system to identify and neutralize foreign objects, such as bacteria and viruses. A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H L$ $C_H 2$, and $C_H 3$) regions, and each light chain contains one N-terminal variable ($V_L$) region and one C-terminal constant ($C_L$) region. Immunoglobulin light chains can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. $V_H$ and $V_L$ regions have the same general structure, with each region comprising four framework (FW or FR) regions, connected by three complementarity determining regions (CDRs). The term "framework region," as used herein, refers to the relatively conserved amino acid sequences within the variable region which are located between the hypervariable or complementary determining regions (CDRs). In a typical immunoglobulin, there are four framework regions in each variable domain, which are designated FR1, FR2, FR3, and FR4. The framework regions form β sheets that provide the structural framework of a variable region (see, e.g., C. A. Janeway et al. (eds.), *Immunobiology*, 5th Ed., Garland Publishing, New York, N.Y. (2001)).

In a typical immunoglobulin, there are three complementary determining regions (CDRs) in each variable domain, which are designated CDR1, CDR2, and CDR3. The CDRs form the "hypervariable region" of an antibody, which is responsible for antigen binding. The CDRs form loops connecting, and in some cases comprising part of, the β-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The disclosure provides, at least in part, antibody agents that bind to PD-1. As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')$_2$ fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g.)Probodies®); Small Modular ImmunoPharmaceuticals ("SMIPs™"); single chain or Tandem diabodies) (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload[e.g., a detectable moiety, a therapeutic moiety, a catalytic moiety, etc], or other pendant group [e.g., poly-ethylene glycol, etc.]). In many embodiments, an antibody agent is or comprises a polypeptide whose amino acid sequence includes one or more structural elements recognized by those skilled in the art as a complementarity determining region (CDR); in some embodiments, an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

In some embodiments, an anti-PD-1 antibody agent comprises an immunoglobulin heavy chain polypeptide and/or immunoglobulin light chain polypeptide. As discussed above, programmed death 1 (PD-1) (also known as programmed cell death 1) is a 268 amino acid type I transmembrane protein (Ishida et al, supra). PD-1 is a member of the CD28/CTLA-4 family of T-cell regulators and is expressed on activated T-cells, B-cells, and myeloid lineage cells (Greenwald et al., supra; and Sharpe et al., supra). PD-1 includes an extracellular IgV domain followed by short extracellular stalk, a transmembrane region and an intracellular tail. The intracellular tail contains two phosphorylation sites located in an immunoreceptor tyrosine-based inhibitory motif and an immunoreceptor tyrosine-based switch motif, which play a role in the ability of PD-1 to negatively regulate T-cell receptor signaling (see, e.g., Ishida et al., supra; and Blank et al., supra).

Certain other antibodies which bind to PD-1, and components thereof, are known in the art (see, e.g., U.S. Pat. No. 8,168,757; Topalian et al, supra; and Patnaik et al, supra). Certain anti-PD-1 antibodies also are commercially available from sources such as, for example, Abcam (Cambridge, Mass.).

In some embodiments, a provided heavy chain, light chain and/or antibody agent is glycosylated and one or more sites. As used herein, "glycan" is a sugar polymer (moiety) component of a glycoprotein. The term "glycan" encompasses free glycans, including glycans that have been cleaved or otherwise released from a glycoprotein. In some embodiments, a glycan is N-linked to an Fc region. In some embodiments, an antibody agent is glycosylated at Asn297 (Kabat numbering).

In some embodiments, present disclosure provides a composition comprising one or more glycoforms of a heavy chain, light chain, and/or antibody agent as described herein. The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform." In some embodiments, a provided composition comprises a plurality of glycoforms of one or more of a heavy chain, light chain, and/or antibody agent as described herein. In some embodiments, a provided composition comprises a plurality of such glycoforms, present in specified absolute and/or relative amounts. In some embodiments, the present disclosure provides compositions that may be substantially free of one or more particular glycoforms of a heavy chain, light chain, and/or antibody agent as described herein.

In some embodiments, an amount of a glycoform is expressed as a "percent." For any given parameter, "percent" refers to the number of moles of a particular glycan (glycan X) relative to total moles of glycans of a preparation. In some embodiments, "percent" refers to the number of moles of PNGase F-released Fc glycan X relative to total moles of PNGase F-released Fc glycans detected.

In some embodiments, a provided heavy chain, light chain and/or antibody agent has a structure that includes one or more disulfide bonds. In some embodiments, the one or more disulfide bonds are at the expected position for an IgG4 immunglobulin. In some embodiments, a disulfide bond is present at one or more residues corresponding to positions selected from residue 22, 96, 130, 143, 199, 222, 225, 257, 317, 363 and 421 of SEQ ID NO: 1. In some embodiments, a disulfide bond is present at one or more residues corresponding to positions selected from residue 23, 88, 134, 194 and 214 of SEQ ID NO: 2.

In some embodiments, an isolated immunoglobulin heavy chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 1 or 5.

In some embodiments, an isolated immunoglobulin light chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 2 or 6.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are disclosed in, for example, Altschul et al, J. Molecular Biol, 215(3): 403-410 (1990), Beigert et al, Proc. Natl. Acad. Sci. USA, 106(10): 3770-3775 (2009), Durbin et al, eds., Biological Sequence Analysis: Probalistic Models of Proteins and Nucleic Acids, Cambridge University Press, Cambridge, UK (2009), Soding, Bioinformatics, 21(1): 951-960 (2005), Altschul et al, Nucleic Acids Res., 25(11): 3389-3402 (1997), and Gusfield, Algorithms on Strings, Trees and Sequences, Cambridge University Press, Cambridge UK (1997)).

One or more amino acids of the aforementioned immunoglobulin heavy chain polypeptides and/or light chain polypeptides can be replaced or substituted with a different amino acid. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

An amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free—OH can be maintained, and glutamine for asparagine such that a free—$NH_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

The present disclosure provides, at least in part, an isolated anti-PD-1 antibody agent comprising, consisting essentially of, or consisting of an inventive isolated amino acid sequences described herein. As used herein, the term "isolated" (or "purified") refers to a nucleic acid sequence (e.g., a polynucleotide) or an amino acid sequence (e.g., a polypeptide) that is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free, or at least 98% free, or at least 99% free from other components present in natural environment of the indicated nucleic acid sequence or amino acid sequence.

By "programmed death 1 (PD-1)-binding agent" is meant a molecule, preferably a proteinaceous molecule, that binds specifically to the programmed death 1 protein (PD-1). In some embodiments, a PD-1-binding agent is an anti-PD-1 antibody agent. In some embodiments, an isolated anti-PD-1 antibody agent comprises, consists essentially of, or consists of an immunoglobulin heavy chain polypeptide (e.g., SEQ ID NO:1) and/or an immunoglobulin light chain polypeptide (e.g., SEQ ID NO:2). In some embodiments, an isolated anti-PD-1 antibody agent comprises, consists essentially of, or consists of an immunoglobulin heavy chain polypeptide whose sequence comprises SEQ ID NO:1 and an immunoglobulin light chain polypeptide whose sequence comprises SEQ ID NO:2.

In some embodiments, a provided polypeptide or heavy chain polypeptide consists essentially of an amino acid sequence of SEQ ID NO: 1 or SEQ ID NO: 5, and may further comprise additional components that do not materially affect the polypeptide, e.g., by influencing affinity of an inventive heavy chain polypeptide to PD-1. Examples of such components include, for example, protein moieties such as biotin that facilitate purification or isolation, passenger mutations, sequences free of problematic sites including free cysteines, additional glycosylation sites, and high-likelihood deamidation or isomerization sites.

In some embodiments, a provided polypeptide or immunoglobulin heavy chain polypeptide consists of an amino acid sequence of SEQ ID NO: 1 or SEQ ID NO: 5 and does not comprise any additional components (i.e., components that are not endogenous to an inventive immunoglobulin heavy chain polypeptide).

In some embodiments, anti-PD-1 antibody agents include variants where one or more amino acids in the immunoglobulin heavy chain polypeptide and/or the immunoglobulin light chain polypeptide are replaced, in any combination, with a different amino acid residue, or can be deleted or inserted, so long as the biological activity of is not materially diminished (e.g., enhanced or improved) as a result of the amino acid replacements, insertions, and/or deletions. The "biological activity" of an anti-PD-1 antibody agent refers to, for example, binding affinity for PD-1 or a particular PD-1 epitope, neutralization or inhibition of PD-1 protein binding to its ligands PD-L1 and PD-L2, neutralization or inhibition of PD-1 protein activity in vivo (e.g., $IC_{50}$), pharmacokinetics, and cross-reactivity (e.g., with non-human homologs or orthologs of the PD-1 protein, or with other proteins or tissues). Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or Kinetic Exclusion Assay (KINEXA™), in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of an anti-PD-1 antibody agent, refer to the ability to substantially antagonize, prohibit, prevent, restrain, slow, disrupt, alter, eliminate, stop, or reverse the progression or severity of, for example, the biological activity of a PD-1 protein, or a disease or condition associated with an PD-1 protein. In some embodiment, an isolated PD-1-binding agent inhibits or neutralizes the activity of a PD-1 protein by at least about 20%, about 30%, about 40%, about 50%, about 60%, about 70%, about 80%, about 90%, about 95%, about 98%, about 99%, about 100%, or a range defined by any two of the foregoing values (e.g., 20% to 100%, 40% to 100% or 60% to 95%, etc.)

In some embodiments, an anti-PD-1 antibody agent is a whole antibody or a fragment thereof (e.g., an antibody fragment). In some embodiments, the antibody or antibody fragment comprises a heavy chain constant region that is based upon wild-type IgG1, IgG2, or IgG4 antibodies, or variants thereof. It will be appreciated that each antibody class, or isotype, engages a distinct set of effector mechanisms for disposing of or neutralizing antigen once recognized. As such, in some embodiments, when an anti-PD-1 antibody agent is an antibody, it can exhibit one or more effector functions, such as participation in antibody-dependent complement-mediated lysis or antibody-dependent cellular toxicity via interactions with effector molecules and cells (e.g., activation of the complement system).

In some embodiments, an anti-PD-1 antibody agent comprises an IgG4 heavy chain constant region. In some embodiments, an anti-PD-1 antibody agent comprises one or more mutations within the IgG heavy chain region. In some embodiments, an anti-PD-1 antibody agent comprises an IgG4 heavy chain constant region having one or more mutations in the heavy chain constant region. In some embodiments, an anti-PD-1 antibody agent comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include an S228P mutation or a serine to proline stabilizing mutation that prevents half molecule exchange with other IgG4 molecules. See, e.g., J. Biol. Chem. 2015; 290(9):5462-5469.

An anti-PD-1 antibody agent also can be an antibody conjugate. In this respect, an anti-PD-1 antibody agent can be a conjugate of (1) an anti-PD-1 antibody and (2) a protein or non-protein moiety. For example, an anti-PD-1 antibody agent an anti-PD-1 antibody conjugated to a peptide, a fluorescent molecule, or a chemotherapeutic agent.

An anti-PD-1 antibody agent can be, or can be obtained from, a human antibody, a non-human antibody, or a chimeric antibody. By "chimeric" is meant an antibody or fragment thereof comprising both human and non-human regions. In some embodiments, an anti-PD-1 antibody agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In some embodiments, CDRH3 of an anti-PD-1 antibody agent is obtained or derived from a mouse monoclonal antibody, while the remaining variable regions and constant region of antibody agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Kohler and Milstein, Eur. J. Immunol., 5: 511-519 (1976); Harlow and Lane (eds.), Antibodies: A Laboratory Manual, CSH Press (1988); and Janeway et al. (eds.), Immunobiology, 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, Nat. Biotechnol., 23(9): 1117-25 (2005), and Lonberg, Handb. Exp. Pharmacol., 181: 69-97 (2008)). A humanized antibody can be generated using any suitable method known in the art (see, e.g., An, Z. (ed.), Therapeutic Monoclonal Antibodies: From Bench to Clinic, John Wiley & Sons, Inc., Hoboken, N.J. (2009)), including, e.g., grafting of non-human CDRs onto a human antibody scaffold (see, e.g., Kashmiri et al, Methods, 36(1): 25-34 (2005); and Hou et al, J. Biochem., 144(1): 115-120 (2008)). In some embodiments, a humanized antibody can be produced using the methods described in, e.g., U.S. Patent Application Publication 2011/0287485 A1.

In some embodiments, an anti-PD-1 antibody agent binds an epitope of PD-1 which blocks the binding of PD-1 to any one or more of its putative ligands. In some embodiments, an anti-PD-1 antibody agent binds an epitope of PD-1 which blocks the binding of PD-1 to two or more of its putative ligands. In a preferred embodiment, an anti-PD-1 antibody agent binds an epitope of a PD-1 protein which blocks the binding of PD-1 to PD-L1 and/or PD-L2.

The disclosure also provides one or more isolated or purified nucleic acid sequences that encode an inventive immunoglobulin heavy chain polypeptide, an inventive immunoglobulin light chain polypeptide, and/or an inventive anti-PD-1 antibody agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like). Nucleic acid sequences encoding an inventive immunoglobulin heavy chain polypeptides include, for example, SEQ ID NO: 3. Nucleic acid sequences encoding an inventive immunoglobulin light chain polypeptides include, for example, SEQ ID NO: 4.

The disclosure further provides a vector comprising one or more nucleic acid sequences encoding a PD-1-binding immunoglobulin heavy chain polypeptide, a PD-1-binding immunoglobulin light chain polypeptide, and/or an anti-PD-1 antibody agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al, *Current Protocols in Molecular Biology*, Greene Publishing Associates and John Wiley & Sons, New York, N.Y. (1994)).

In addition to the nucleic acid sequence encoding an inventive polypeptide, an inventive immunoglobulin heavy polypeptide, an inventive immunoglobulin light chain polypeptide, and/or an inventive—anti-PD-1 antibody agent, the vector can comprise expression control sequences, such as promoters, enhancers, polyadenylation signals, transcription terminators, signal peptides (e.g., the osteonectin signal peptide), internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al, Proc. Natl. Acad. Sci., 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al, Nuc. Acid. Res., 27: 4324-4327 (1999); Nuc. Acid. Res., 28: e99 (2000); U.S. Pat. No. 7,112,715; and Kramer & Fussenegger, Methods Mol. Biol, 308: 123-144 (2005)).

The term "enhancer" as used herein, refers to a DNA sequence that increases transcription of, for example, a nucleic acid sequence to which it is operably linked.

Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al, *Proc. Natl. Acad. Sci. USA*, 77: 3567-3570 (1980); O'Hare et al, *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al, *J. Mol. Biol.*, 150: 1-14 (1981); Santerre et al, *Gene*, 30: 147-156 (1984); Kent et al, *Science*, 237: 901-903 (1987); Wigler et al, *Cell*, 11: 223-232 (1977); Szybalska & Szybalski, *Proc. Natl. Acad. Sci. USA*, 48: 2026-2034 (1962); Lowy et al, *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al, Gene Therapy, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Life Technologies (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), UCOE from Millipore (Billerica, Mass.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Nucleic acid sequences encoding inventive amino acid sequences can be provided to a cell on the same vector (i.e., in cis). A unidirectional promoter can be used to control expression of each nucleic acid sequence. In some embodiments, a combination of bidirectional and unidirectional promoters can be used to control expression of multiple nucleic acid sequences. Nucleic acid sequences encoding inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding inventive amino acid sequences can be introduced into a host cell that is capable of expressing the polypeptides encoded thereby, including any suitable prokaryotic or eukaryotic cell. As such, the present disclosure provides an isolated cell comprising an inventive vector. Host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Envinia*. Useful prokaryotic cells include, for example, the various strains of *Escherichia coli* (e.g., K12, HB101 (ATCC No. 33694), DH5α, DH10, MC1061 (ATCC No. 53338), and CC102).

In some embodiments, an inventive vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhino-sporidium, Saccharomyces*, and *Schizosaccharomyces*. Yeast cells include, for example, *Saccharomyces cerivisae* and *Pichia pastoris*.

Suitable insect cells are described in, for example, Kitts et al, *Biotechniques,* 14: 810-817 (1993); Lucklow, *Curr. Opin. Biotechnol.,* 4: 564-572 (1993); and Lucklow et al, *J. Virol.,* 67: 4566-4579 (1993). Insect cells include, for example, Sf-9 and HI5 (Invitrogen, Carlsbad, Calif.).

In some embodiments, mammalian cells are utilized. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al, Proc. Natl. Acad. Sci. USA, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70).

Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al, Proc. Natl. Acad. Sci. USA, 85: 1581-1585 (1988)), Raji cells (CCL-86), PER.C6 cells (Crucell Holland B.V., Leiden, The Netherlands), and derivatives thereof.

A nucleic acid sequence encoding an inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7*, Gene Transfer and Expression Protocols, Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al, *Mol. Cell Biol,* 7: 2031-2034 (1987)). Phage or viral vectors can be introduced into host cells, after growth of infectious particles in suitable packaging cells, many of which are commercially available.

The disclosure provides a composition comprising an effective amount of an inventive immunoglobulin heavy chain polypeptide, an inventive immunoglobulin light chain polypeptide, an anti-PD-1 antibody agent, a nucleic acid sequence encoding any of the foregoing, or a vector comprising the nucleic acid sequence. In some embodiments, a composition is pharmaceutically acceptable (e.g., physiologically acceptable) composition, which comprises a carrier, preferably a pharmaceutically acceptable (e.g., physiologically acceptable) carrier, and an inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: The Science and Practice of Pharmacy, 21st Edition, Lippincott Williams & Wilkins, Philadelphia, Pa. (2001).

The disclosure further provides methods of treating any disease or disorder in which expression, improper expression (e.g., overexpression) or increased activity of a PD-1 protein causes or contributes to the pathological effects of the disease, or a decrease in PD-1 protein levels or activity has a therapeutic benefit in mammals, such as humans. The disclosure also provides a method of treating a cancer or an infectious disease in a mammal. Mammals include, e.g., mice, rats, rabbits, dogs, cats, cows, horses, non-human primates, and humans. The method comprises administering the aforementioned composition to a mammal having a cancer or an infectious disease, whereupon the cancer or infectious disease is treated in the mammal. As discussed herein, PD-1 is abnormally expressed in a variety of cancers (see, e.g., Brown et al, J. Immunol., 170: 1257-1266 (2003); and Flies et. al, Yale Journal of Biology and Medicine, 84:

409-421 (2011)), and PD-L1 expression in some renal cell carcinoma patients correlates with tumor aggressiveness.

The disclosure further provides methods of enhancing an immune response or increasing the activity of an immune cell in a mammal having a disorder that is responsive to PD-1 inhibition. In some embodiments, such methods include administering an effective amount of any PD-1 binding agent or antibody agent described herein. In some embodiments, administration of a PD-1 binding agent enhances or increases an immune response or immune cell activity in a mammal or tissue thereof. In some embodiments, an immune response is a humoral or cell mediated immune response. In some embodiments, an immune response is a CD4 or CD8 T cell response. In some embodiments, an immune response is a B cell response.

Inventive methods and compositions described herein can be used to treat any type of cancer known in the art, such as, for example, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, adenocarcinoma (e.g., adenocarcinoma of the lung), or Merkel cell carcinoma (see, e.g., Bhatia et al., Curr. Oncol. Rep., 13(6): 488-497 (2011)). In some embodiments, a cancer is endometrial cancer, breast cancer, ovarian cancer, cervical cancer, fallopian tube cancer, testicular cancer, primary peritoneal cancer, colon cancer, colorectal cancer, stomach cancer, small intestine cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, adenocarcinoma, adenocarcinoma of the lung, prostate cancer, pancreatic cancer, mesothelioma, Merkel cell carcinoma, sarcoma, glioblastoma, or hematological cancer (e.g., multiple myeloma, B-cell lymphoma, T-cell lymphoma, Hodgkin's lymphoma/primary mediastinal B-cell lymphoma, or chronic myelogenous leukemia). In some embodiments, a cancer to be treated with the inventive methods and/or compositions described herein is characterized by microsatellite instability or lack thereof. Microsatellite instability ("MSI") is or comprises a change that in the DNA of certain cells (such as tumor cells) in which the number of repeats of microsatellites (short, repeated sequences of DNA) is different than the number of repeats that was contained in the DNA from which it was inherited. Microsatellite instability arises from a failure to repair replication-associated errors due to a defective DNA mismatch repair (MMR) system. This failure allows persistence of mismatch mutations all over the genome, but especially in regions of repetitive DNA known as microsatellites, leading to increased mutational load. It has been demonstrated that at least some tumors characterized by MSI-H have improved responses to certain anti-PD-1 agents (Le et al., (2015) *N. Engl. J. Med.* 372(26): 2509-2520; Westdorp et al., (2016) *Cancer Immunol. Immunother.* 65(10):1249-1259).

In some embodiments, a cancer has a microsatellite instability status of high microsatellite instability (e.g., MSI-H status). In some embodiments, a cancer has a microsatellite instability status of low microsatellite instability (e.g., MSI-L status). In some embodiments, a cancer has a microsatellite instability status of microsatellite stable (e.g., MSS status). In some embodiments microsatellite instability status is assessed by a next generation sequencing (NGS)-based assay, an immunohistochemistry (IHC)-based assay, and/or a PCR-based assay. In some embodiments, microsatellite instability is detected by NGS. In some embodiments, microsatellite instability is detected by IHC. In some embodiments, microsatellite instability is detected by PCR.

In embodiments, the cancer is associated with a high tumor mutation burden (TMB). In some embodiments, the cancer is associated with high TMB and MSI-H. In some embodiments, the cancer is associated with high TMB and MSI-L or MSS. In some embodiments, the cancer is endometrial cancer associated with high TMB. In some related embodiments, the endometrial cancer is associated with high TMB and MSI-H. In some related embodiments, the endometrial cancer is associated with high TMB and MSI-L or MSS.

In some embodiments, a cancer is a mismatch repair deficient cancer. Microsatellite instability may arise from a failure to repair replication-associated errors due to a defective DNA mismatch repair (MMR) system. This failure allows persistence of mismatch mutations all over the genome, but especially in regions of repetitive DNA known as microsatellites, leading to increased mutational load that may improve responses to certain anti-PD-1 agents. Id. In some embodiments, a cancer is a hypermutated cancer. In some embodiments, a cancer harbors a mutation in polymerase epsilon (POLE).

The inventive methods can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)).

The inventive methods can be used to treat any type of autoimmune disease (i.e., as disease or disorder caused by immune system over-activity in which the body attacks and damages its own tissues), such as those described in, for example, MacKay I. R. and Rose N. R., eds., *The Autoimmune Diseases, Fifth Edition*, Academic Press, Waltham, Mass. (2014). Examples of autoimmune diseases that can be treated by the inventive method include, but are not limited to, multiple sclerosis, type 1 diabetes mellitus, rheumatoid arthritis, scleroderma, Crohn's disease, psoriasis, systemic lupus erythematosus (SLE), and ulcerative colitis.

Administration of a composition comprising an inventive immunoglobulin heavy chain polypeptide, an inventive immunoglobulin light chain polypeptide, an inventive PD-1-binding agent, an inventive nucleic acid sequence encoding any of the foregoing, or an inventive vector comprising an inventive nucleic acid sequence induces an immune response against a cancer or infectious disease in a mammal. Mammals include, e.g., mice, rats, rabbits, dogs, cats, cows, horses, non-human primates, and humans. An "immune response" can entail, for example, antibody production and/or the activation of immune effector cells (e.g., T-cells).

As used herein, the terms "treatment," "treating," and the like refer to obtaining a desired pharmacologic and/or physiologic effect. In some embodiments, the effect is therapeutic, i.e., the effect partially or completely cures a disease and/or adverse symptom attributable to the disease. To this end, the inventive method comprises administering a "therapeutically effective amount" of the PD-1-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the PD-1-binding agent to elicit a desired response in the individual. For example, a therapeutically effective amount of a PD-1-binding agent is an amount which decreases PD-1 protein bioactivity in a human and/or enhances the immune response against a cancer or infectious disease.

Additionally or alternatively, the pharmacologic and/or physiologic effect may be prophylactic, i.e., the effect completely or partially prevents a disease or symptom thereof. In this respect, the inventive method comprises administering a "prophylactically effective amount" of an anti-PD-1 antibody agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values). In some embodiments, from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values). In some embodiments, from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values). In some embodiments, from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

Composition(s) comprising an effective amount of an inventive immunoglobulin heavy chain polypeptide, an inventive immunoglobulin light chain polypeptide, an inventive PD-1-binding agent, an inventive nucleic acid sequence encoding any of the foregoing, or an inventive vector comprising an inventive nucleic acid sequence can be administered to a mammal using standard administration techniques, including oral, ocular, parenteral, intravenous, intraperitoneal, subcutaneous, pulmonary, bronchial, buccal, intradermal, interdermal, transdermal, topical, intramuscular, intranasal, buccal, sublingual, enteral, intra-arterial, intragastric, within a specific organ (e.g., intrahepatic), rectally, subcutaneously, sublingual, tracheal, vaginal, vitreal, intramedullar, intrathecal, intraventricular, mucosal or suppository administration. In some embodiments, a composition is suitable for parenteral administration. The term "parenteral," as used herein, includes intravenous, intramuscular, subcutaneous, rectal, vaginal, and intraperitoneal administration. In some embodiments, the composition is administered to a mammal using peripheral systemic delivery by intravenous, intraperitoneal, or subcutaneous injection. Mammals include, e.g., mice, rats, rabbits, dogs, cats, cows, horses, non-human primates, and humans.

Once administered to a mammal (e.g., a human), the biological activity of an anti-PD-1 antibody agent can be measured by any suitable method known in the art. For example, the biological activity can be assessed by determining the stability of a particular PD-1-binding agent. In some embodiments, an anti-PD-1 antibody agent has an in vivo half-life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In some embodiments, an anti-PD-1 antibody agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In some embodiments, the PD-1-binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The stability of an anti-PD-1 antibody agent can be measured using any other suitable assay known in the art, such as, for example, measuring serum half-life, differential scanning calorimetry (DSC), thermal shift assays, and pulse-chase assays. Other methods of measuring protein stability in vivo and in vitro that can be used in the context of the invention are described in, for example, *Protein Stability and Folding*, B. A. Shirley (ed.), Human Press, Totowa, N.J. (1995); *Protein Structure, Stability, and Interactions (Methods in Molecular Biology)*, Shiver J. W. (ed.), Humana Press, New York, N.Y. (2010); and Ignatova, *Microb. Cell Fact.*, 4: 23 (2005).

The stability of an anti-PD-1 antibody agent can be measured in terms of the transition mid-point value ($T_m$), which is the temperature where 50% of the amino acid sequence is in its native confirmation, and the other 50% is denatured. In general, the higher the $T_m$, the more stable the protein. In some embodiments, an inventive PD-1 binding agent comprises a transition mid-point value ($T_m$) in vitro of about 60-100° C. For example, an anti-PD-1 antibody agent can comprise a $T_m$ in vitro of about 65-80° C. (e.g., 66° C., 68° C., 70° C., 71° C., 75° C., or 79° C.), about 80-90° C. (e.g., about 81° C., 85° C., or 89° C.), or about 90-100° C. (e.g., about 91° C., about 95° C., or about 99° C.).

The biological activity of a particular anti-PD-1 antibody agent also can be assessed by determining its binding affinity to a PD-1 protein or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (µM) (e.g., from about 1 picomolar (pM) to about 1 nanomolar (nM), from about 1 nM to about 1 micromolar (µM), or from about 1 µM to about 100 µM). In some embodiments, the PD-1-binding agent can bind to an PD-1 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In some embodiments, the PD-1-binding agent can bind to PD-1 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, e.g., Janeway et al. (eds.), Immunobiology, 5th ed., Garland Publishing, New York, N.Y., 2001).

An anti-PD-1 antibody agent may be administered alone or in combination with other drugs (e.g., as an adjuvant). For example, a PD-1-binding agent can be administered in combination with other agents for the treatment or prevention of the diseases disclosed herein, such as agents that are cytotoxic to cancer cells, modulate the immunogenicity of cancer cells, or promote immune responses to cancer cells. In this respect, for example, an anti-PD-1 antibody agent can be used in combination with at least one other anticancer agent including, for example, any chemotherapeutic agent known in the art, ionization radiation, small molecule anti-cancer agents, cancer vaccines, biological therapies (e.g., other monoclonal antibodies, cancer-killing viruses, gene therapy, and adoptive T-cell transfer), and/or surgery. In some embodiments, a subject (e.g., a mammal, e.g., a human) for treatment with an anti-PD-1 antibody agent has been treated or will be treated with chemotherapy (e.g., platinum-based chemotherapy). In some embodiments, a chemotherapeutic agent is actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, or vinorelbine. In some such embodiments, a chemotherapeutic agent is a platinum-based chemotherapeutic agent, such as cisplatin, carboplatin, oxaliplatin, nedaplatin, triplatin tetranitrate, phenanthriplatin, picoplatin, or satraplatin. In some such embodiments, a chemotherapeutic agent is a folate antimetabolite such as pemetrexed. In some embodiments, a subject (e.g., a mammal, e.g. a human) for treatment with an anti-PD-1 antibody agent has been treated or will be treated with an anti-angiogenic agent, for example, bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor (e.g. peptide troponin I and chondromodulin I), matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, interferon beta, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, RO4929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, Flt2-11, CBO-P11, Je-11, V1, and any combination thereof. In some embodiments, an anti-PD-1 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

In some embodiments, an anti-PD-1 antibody agent is used to treat an infectious disease. When the inventive method treats an infectious disease, an anti-PD-1 antibody agent can be administered in combination with at least one antibacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In some embodiments, an anti-PD-1 antibody agent is used to treat an autoimmune disease. In some embodiments, an autoimmune disease is multiple sclerosis, type 1 diabetes mellitus, rheumatoid arthritis, scleroderma, Crohn's disease, psoriasis, systemic lupus erythematosus (SLE), or ulcerative colitis. When the inventive method treats an autoimmune disease, an anti-PD-1 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

In some embodiments, an anti-PD-1 antibody agent can be administered in combination with other agents that inhibit immune checkpoint pathways. For example, an inventive PD-1 binding agent can be administered in combination with agents that inhibit or antagonize the CTLA-4, TIM-3 or LAG-3 pathways. Combination treatments that simultaneously target two or more of these immune checkpoint pathways have demonstrated improved and potentially synergistic antitumor activity (see, e.g., Sakuishi et al, J. Exp. Med., 207: 2187-2194 (2010); Ngiow et al, Cancer Res., 71: 3540-3551 (2011); and Woo et al., Cancer Res., 72: 917-927 (2012)). In some embodiments, an inventive PD-1 binding agent is administered in combination with an antibody that binds to TIM-3 and/or an antibody that binds to LAG-3. In this respect, the inventive method of treating a cancer or an infectious disease in a mammal can further comprise administering to the mammal a composition comprising (i) an antibody that binds to a TIM-3 protein and (ii) a pharmaceutically acceptable carrier or a composition comprising (i) an antibody that binds to a LAG-3 protein and (ii) a pharmaceutically acceptable carrier. Exemplary antibody agents specific for LAG-3 and TIM-3 are described in WO2016/126858 and WO2016/161270, respectively, both of which are hereby incorporated by reference. In some embodiments, an anti-TIM-3 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

In some embodiments, an anti-PD-1 antibody agent is administered in combination with an agent that inhibits LAG-3 signaling and/or an agent that inhibits TIM-3 signaling. In some embodiments, an anti-PD-1 antibody agent is administered to a subject that has been administered or will be administered an agent that inhibits LAG-3 signaling, such that the subject receives treatment with both. In some embodiments, an anti-PD-1 antibody agent is administered to a subject that has been administered or will be administered an agent that inhibits TIM-3 signaling, such that the subject receives treatment with both. In some embodiments, a mammal that receives treatment an anti-PD-1 antibody agent has been or will receive treatment with an agent that inhibits TIM-3 and an agent that inhibits LAG-3, such that the mammal receives all three. In some embodiments, an anti-PD-1 antibody agent is administered in combination with an antibody that binds to LAG-3 and/or an antibody that binds to TIM-3.

In some embodiments, a subject is receiving or will receive one or more additional therapies in combination with an anti-PD-1 antibody agent. In some embodiments, an additional therapy is a PARP inhibitor. In some embodiments, a PARP inhibitor is ABT-767, AZD 2461, BGB-290, BGP 15, CEP 8983, CEP 9722, DR 2313, E7016, E7449, fluzoparib (SHR 3162), IMP 4297, IN01001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), 0N02231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, a PARP inhibitor is niraparib, olaparib, rucaparib, talazoparib, and veliparib. In some embodiments, additional therapies include treatment with a composition that delivers an agent that inhibits TIM-3 or LAG-3 and treatment with a PARP inhibitor such that the subject receives treatment with all three. In some embodiments, additional therapies include treatment with a composition that delivers an agent that inhibits TIM-3, treatment with a composition that delivers an agent that inhibits LAG-3, and treatment with a PARP inhibitor such that the subject receives treatment with all four.

In addition to therapeutic uses, an anti-PD-1 antibody agent as described herein can be used in diagnostic or research applications. In this respect, an anti-PD-1 antibody agent can be used in a method to diagnose a cancer or infectious disease. In a similar manner, an anti-PD-1 antibody agent can be used in an assay to monitor PD-1 protein levels in a subject being tested for a disease or disorder that is associated with abnormal PD-1 expression. Research applications include, for example, methods that utilize an anti-PD-1 antibody agent and a label to detect a PD-1 protein in a sample, e.g., in a human body fluid or in a cell or tissue extract. An anti-PD-1 antibody agent can be used with or without modification, such as covalent or non-covalent labeling with a detectable moiety. For example, the detectable moiety can be a radioisotope (e.g., $^{3}H$, $^{14}C$, $^{32}P$, $^{35}S$, or $^{125}I$), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al, Nature, 194: 495-496 (1962); David et al, Biochemistry, 13: 1014-1021 (1974); Pain et al, J. Immunol. Meth., 40: 219-230 (1981); and Nygren, J. Histochem. and Cytochem., 30: 407-412 (1982)).

PD-1 protein levels can be measured using an anti-PD-1 antibody agent as described herein using any suitable method known in the art. Such methods include, for example, radioimmunoassay (RIA), and FACS. Normal or standard expression values of PD-1 protein can be established using any suitable technique, e.g., by combining a sample comprising, or suspected of comprising, a PD-1 polypeptide with a PD-1-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, Monoclonal Antibodies: A Manual of Techniques, CRC Press, Inc. (1987)). The amount of PD-1 polypeptide expressed in a sample is then compared with a standard value.

An anti-PD-1 antibody agent can be provided in a kit, i.e., a packaged combination of reagents in predetermined amounts with instructions for performing a diagnostic assay. If the PD-1-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

Other features of the invention will become apparent in the course of the following descriptions of exemplary embodiments, which are given for illustration of the invention and are not intended to be limiting thereof.

Exemplification

EXAMPLE 1

Description of Certain Exemplary Anti-PD-1 Antibodies

This example describes particular anti-PD-1 antibody heavy chain polypeptide and light chain polypeptide sequences and nucleic acids encoding the same.

```
An anti-PD-1 antibody heavy chain polypeptide (CDR sequences)
                                                           (SEQ ID NO: 1)
EVQLLESGGGLVQPGGSLRLSCAASGFTFSSYDMSWVRQAPGKGLEWVS

TISGGGSYTYYQDSVKGRFTISRDNSKNTLYLQMNSLRAEDTAVYYCASP

YYAMDYWGQGTTVTVSSASTKGPSVFPLAPCSRSTSESTAALGCLVKDY

FPEPVTVSWNSGALTSGVHTFPAVLQSSGLYSLSSVVTVPSSSLGTKTYTC
```

```
NVDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK
```

An anti-PD-1 antibody light chain polypeptide (CDR sequences)
(SEQ ID NO: 2)

```
DIQLTQSPSFLSAYVGDRVTITCKASQDVGTAVAWYQQKPGKAPKLLIY

WASTLHTGVPSRFSGSGSGTEFTLTISSLQPEDFATYYCQHYSSYPWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQ

GLSSPVTKSFNRGEC
```

An anti-PD-1 antibody heavy chain polypeptide with a signal sequence
(SEQ ID NO: 5)

```
MEFGLSWLFLVAILKGVQCEVQLLESGGGLVQPGGSLRLSCAASGFTFSS

YDMSWVRQAPGKGLEWVSTISGGGSYTYYQDSVKGRFTISRDNSKNTLY

LQMNSLRAEDTAVYYCASPYYAMDYWGQGTTVTVSSASTKGPSVFPLA

PCSRSTSESTAALGCLVKDYFPEPVTVSWNSGALTSGVHTFPAVLQSSGL

YSLSSVVTVPSSSLGTKTYTCNVDHKPSNTKVDKRVESKYGPPCPPCPAPE

FLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEA

LHNHYTQKSLSLSLGK
```

An anti-PD-1 antibody light chain polypeptide with a signal sequence
(SEQ ID NO: 6)

```
MDMRVPAQLLGLLLLWLPGARCDIQLTQSPSFLSAYVGDRVTITCKASQD

VGTAVAWYQQKPGKAPKWYWASTLHTGVPSRFSGSGSGTEFTLTISSL

QPEDFATYYCQHYSSYPWTFGQGTKLEIKRTVAAPSVFIFPPSDEQLKSGT

ASVVCLLNNFYPREAKVQWKVDNALQSGNSQESVTEQDSKDSTYSLSST

LTLSKADYEKHKVYACEVTHQGLSSPVTKSFNRGEC
```

Nucleotide sequence encoding anti-PD-1 antibody heavy chain polypeptide
(SEQ ID NO: 3)

```
GAG GTG CAG CTG TTG GAG TCT GGG GGA GGC TTG GTA CAG CCT

GGG GGG TCC CTG AGA CTC TCC TGT GCA GCC TCT GGA TTC ACT

TTC AGT AGC TAT GAC ATG TCT TGG GTC CGC CAG GCT CCA GGG

AAG GGG CTG GAG TGG GTC TCA ACC ATT AGT GGT GGT GGT AGT

TAC ACC TAC TAT CAA GAC AGT GTG AAG GGG CGG TTC ACC ATC

TCC AGA GAC AAT TCC AAG AAC ACG CTG TAT CTG CAA ATG AAC

AGC CTG AGA GCC GAG GAC ACG GCC GTA TAT TAC TGT GCG TCC

CCT TAT TAT GCT ATG GAC TAC TGG GGG CAA GGG ACC ACG GTC

ACC GTC TCC TCA GCA TCC ACC AAG GGC CCA TCG GTC TTC CCG

CTA GCA CCC TGC TCC AGG AGC ACC TCC GAG AGC ACA GCC GCC

CTG GGC TGC CTG GTC AAG GAC TAC TTC CCC GAA CCA GTG ACG
```

```
GTG TCG TGG AAC TCA GGC GCC CTG ACC AGC GGC GTG CAC ACC

TTC CCG GCT GTC CTA CAG TCC TCA GGA CTC TAC TCC CTC AGC

AGC GTG GTG ACC GTG CCC TCC AGC AGC TTG GGC ACG AAG ACC

TAC ACC TGC AAC GTA GAT CAC AAG CCC AGC AAC ACC AAG GTG

GAC AAG AGA GTT GAG TCC AAA TAT GGT CCC CCA TGC CCA CCA

TGC CCA GCA CCT GAG TTC CTG GGG GGA CCA TCA GTC TTC CTG

TTC CCC CCA AAA CCC AAG GAC ACT CTC ATG ATC TCC CGG ACC

CCT GAG GTC ACG TGC GTG GTG GTG GAC GTG AGC CAG GAA GAC

CCC GAG GTC CAG TTC AAC TGG TAC GTG GAT GGC GTG GAG GTG

CAT AAT GCC AAG ACA AAG CCG CGG GAG GAG CAG TTC AAC AGC

ACG TAC CGT GTG GTC AGC GTC CTC ACC GTC CTG CAC CAG GAC

TGG CTG AAC GGC AAG GAG TAC AAG TGC AAG GTC TCC AAC AAA

GGC CTC CCG TCC TCC ATC GAG AAA ACC ATC TCC AAA GCC AAA

GGG CAG CCC CGA GAG CCA CAG GTG TAC ACC CTG CCC CCA TCC

CAG GAG GAG ATG ACC AAG AAC CAG GTC AGC CTG ACC TGC CTG

GTC AAA GGC TTC TAC CCC AGC GAC ATC GCC GTG GAG TGG GAG

AGC AAT GGG CAG CCG GAG AAC AAC TAC AAG ACC ACG CCT CCC

GTG CTG GAC TCC GAC GGC TCC TTC TTC CTC TAC AGC AGG CTA

ACC GTG GAC AAG AGC AGG TGG CAG GAG GGG AAT GTC TTC TCA

TGC TCC GTG ATG CAT GAG GCT CTG CAC AAC CAC TAC ACA CAG

AAG AGC CTC TCC CTG TCT CTG GGT AAA
```

Nucleotide sequence encoding an anti-PD-1 antibody light chain polypeptide
(SEQ ID NO: 4)

```
GAC ATC CAG TTG ACC CAG TCT CCA TCC TTC CTG TCT GCA TAT

GTA GGA GAC AGA GTC ACC ATC ACT TGC AAG GCC AGT CAG GAT

GTG GGT ACT GCT GTA GCC TGG TAT CAG CAA AAA CCA GGG AAA

GCC CCT AAG CTC CTG ATC TAT TGG GCA TCC ACC TGC ACA CT

GGG GTC CCA TCA AGG TTC AGC GGC AGT GGA TCT GGG ACA GAA

TTC ACT CTC ACA ATC AGC AGC CTG CAG CCT GAA GAT TTT GCA

ACT TAT TAC TGT CAG CAT TAT AGC AGC TAT CCG TGG ACG TTT

GGC CAG GGG ACC AAG CTG GAG ATC AAA CGG ACT GTG GCT GCA

CCA TCT GTC TTC ATC TTC CCG CCA TCT GAT GAG CAA TTG AAA

TCT GGA ACT GCC TCT GTT GTG TGC CTG CTG AAT AAC TTC TAT

CCC AGA GAG GCC AAA GTA CAG TGG AAG GTG GAT AAC GCC CTC

CAA TCG GGT AAC TCC CAG GAG AGT GTC ACA GAG CAG GAC AGC

AAG GAC AGC ACC TAC AGC CTC AGC AGC ACC CTG ACG CTG AGC

AAA GCA GAC TAC GAG AAA CAC AAA GTC TAC GCC TGC GAA GTC

ACC CAT CAG GGC CTC AGC TCG CCC GTC ACA AAG AGC TTC AAC

AGG GGA GAG TGT
```

The sequences above describe an exemplary humanized monoclonal anti-PD-1 antibody utilizing a human IGHG4*01 heavy chain gene, and a human IGKC*01 kappa light chain gene, as scaffolds. There is a single Ser to Pro point mutation in the hinge region of the IgG4 heavy chain. This mutation is at the canonical S228 position, corresponding to residue 243 in SEQ ID NO: 5, which includes the signal sequence. Without wishing to be bound by theory, it is envisioned that this point mutation serves to stabilize the hinge of the antibody heavy chain.

Biophysical and biochemical characterization of this exemplary humanized monoclonal anti-PD-1 antibody is consistent with the expected disulfide linkage pattern for an IgG4 molecule. The residues involved in the expected inter- and intrachain disulfide linkages are tabulated below (Tables 1 and 2).

TABLE 1

Expected residues involved in disulfide linkages of an exemplary anti-PD-1 antibody agent heavy chain having an amino acid sequence as set forth in SEQ ID NO: 1.

| Cysteine residue ID after Edelman[a] | anti-PD-1 mAb HC Residue (position in SEQ ID NO: 1) |
|---|---|
| I | 22 |
| II | 96 |
| III | 130 |
| IV | 143 |
| V | 199 |
| VI | 222 |
| VII | 225 |
| VIII | 257 |
| IX | 317 |
| X | 363 |
| XI | 421 |

TABLE 2

Expected residues involved in disulfide linkages of an exemplary anti-PD-1 antibody agent light chain having an amino acid sequence as set forth in SEQ ID NO: 2.

| Cysteine residue ID after Edelman[a] | anti-PD-1 mAb LC Residue (position in SEQ ID NO: 2) |
|---|---|
| I | 23 |
| II | 88 |
| III | 134 |
| IV | 194 |
| V | 214 |

This exemplary anti-PD-1 antibody exhibits an occupied N-glycosylation site at asparagine residue 293 in the CH2 domain of each heavy chain in the mature protein sequence (SEQ ID NO:1). The expressed N-glycosylation at this site is a mixture of oligosaccharide species typically observed on IgGs expressed in mammalian cell culture, for example, shown below is the relative abundance of glycan species from a preparation of this exemplary anti-PD-1 antibody cultured in Chinese Hamster Ovary (CHO) cells (Table 3).

TABLE 3

Glycan Analysis of an anti-PD-1 antibody binding agent

| Species | Abundance (% of total oligosaccharide) | Description of Glycan |
|---|---|---|
| G0 | <0.1% | Nonfucosylated agalactobiantennary complex-type oligosaccharide |
| G0F | 19.5% | Core fucosylated agalactobiantennary complex type oligosaccharide |
| G1 | 0.1% | Nonfucosylated monogalactosylated biantennary complex type oligosaccharide |
| G1F | 45.6% | Core fucosylated monogalactosylated biantennary complex type oligosaccharide |
| G2F | 27.4% | Core fucosylated galactosylated biantennary complex type oligosaccharide |
| M5 | 0.5% | Oligomannosidic N-glycan, $Man_5GlcNAc_2$ |

EXAMPLE 2

Binding of an Exemplary Anti-PD-1 Antibody to Recombinant PD-1

This example describes binding of an exemplary anti-PD-1 antibody (having heavy and light chains as set forth in SEQ ID NOs: 1 & 2, respectively) to recombinant PD-1 polypeptides. Specifically, this example demonstrates high affinity binding of an exemplary antibody to soluble PD-1 fusions and cell-expressed recombinant PD-1 as determined using surface plasmon resonance (SPR) and flow cytometry, respectively.

SPR analyses were carried out using a Biacore T200 system and kinetic constants were determined using Biacore T200 Evaluation software. Experimental parameters were chosen such that saturation was reached at the highest antigen concentrations and Rmax values were kept under 100 response units (RU). GE anti-human IgG (Fc-specific) was immobilized on a Biacore CM5 chip. An exemplary anti-PD-1 antibody (having heavy and light chains as set forth in SEQ ID NOs: 1 & 2, respectively) was then captured onto this surface using EDC-activated amine coupling chemistry. Next, dimeric human or cynomolgus monkey PD-1 fusion proteins (fused with mouse IgG2a Fc) in a two-fold serial dilution series were flowed over the captured exemplary antibody and dissociation was monitored. Capture and analyte binding were performed in HBS-EP+ buffer. Chips were regenerated between each run using 3 M $MgCl_2$. The resulting sensorgrams were fitted globally using a 1:1 binding model to calculate on- and off-rates ($k_{assoc}$ and $k_{dissoc}$, respectively) and dissociation constants as a measure of overall affinity ($K_D$). SPR measurements demonstrated that an exemplary anti-PD-1 antibody binds human and cynomolgus PD-1 with a fast association rate, a slow dissociation rate, and a high overall affinity (Table 4). Moreover, binding kinetics to human and cynomolgus monkey PD-1 were similar, with less than a 2-fold difference in $K_D$ values.

Flow cytometry studies were performed with CHO-K1 cell line clones in which either full length native human or cynomolgus monkey PD-1 was stably transfected. An exemplary anti-PD-1 antibody (having heavy and light chains as set forth in SEQ ID NOs: 1 & 2, respectively) was diluted in 3-fold dilutions. Dilutions of exemplary antibody were added to human or cynomolgus monkey PD-1 expressing CHO-K1 cells (1E5 cells) and incubated on ice. Cells were washed twice and incubated on ice with PE-conjugated mouse anti-human IgG4 to detect antibody binding. Cells were washed and resuspended in the presence of propidium iodide to exclude dead cells and fixed and analyzed for fluorescence on a BD FACSArray instrument (BD Biosciences). Data were analyzed for median fluorescence intensity, graphed, and curves fitted for $EC_{50}$ value calculation in GraphPad Prism (GraphPad Software, Inc.) using a non-linear (sigmoidal) regression analysis. This exemplary anti-PD-1 antibody was found to bind to cell-surface human and cynomolgus monkey PD-1 with an $EC_{50}$ of 2.0 and 3.4 nM, respectively (Table 4).

TABLE 4

Binding of exemplary anti-PD-1 antibody to PD-1 by Surface Plasma Resonance (SPR) and PD-1 expressing CHO-K1 cells

| | Kinetic Parameters (SPR) | | | PD-1 expressing CHO-K1 cells |
|---|---|---|---|---|
| Species | $K_{assoc}$ (Ms)$^{-1}$ | $K_{dissoc}$ (s$^{-1}$) | $K_D$ (nM) | $EC_{50}$ (nM) |
| Human | $5.7 \times 10^5$ | $1.7 \times 10^{-4}$ | 0.30 | 2.0 |
| Cynomolgus monkey | $4.3 \times 10^5$ | $2.3 \times 10^{-4}$ | 0.53 | 3.4 |

$K_{assoc}$ = association rate constant; $K_{dissoc}$ = dissociation rate constant; $K_D$ = dissociation constant.

This example demonstrates that anti-PD-1 antibodies within the scope of the present invention can bind to PD-1 polypeptides with high affinity.

EXAMPLE 3

Receptor Occupancy of an Exemplary Anti-PD-1 Antibody

This example describes the ability of an exemplary anti-PD-1 antibody (having heavy and light chains as set forth in SEQ ID NOs: 1 & 2, respectively) to occupy the native PD-1 expressed on human and cynomolgus monkey peripheral blood mononuclear cells (PBMCs).

For these studies, PBMCs from healthy human donors or cynomolgus monkeys were used. Human PBMCs were isolated from buffy coats obtained from the Indiana Blood Center and cynomolgus monkey PBMCs were isolated from peripheral blood collected aseptically into sodium heparin obtained from Worldwide Primates, Inc. In both cases, separation was by Ficoll using Ficoll-Paque 1.077 and cryopreserved for later use.

On the day of the experiments, the cryopreserved cells were thawed and the cell concentration was adjusted to 2E6 cells/ml prior to resting overnight at 37° C. in a humidified $CO_2$ incubator. Cells were then pelleted and re-suspended in 1 ml of media and recounted. The cell concentration was adjusted to 4E5 cells/150 µl of media. Human AB Serum (40 µl/ml) was added to block Fc receptors. After centrifugation, the cells were incubated with exemplary anti-PD-1 antibody at 4° C. PBMCs were then washed three times before being split into two conditions. One set of cells was incubated with exemplary anti-PD-1 antibody and the other set with IgG4 for 30 minutes at 4° C. The PBMCs were then washed four times prior to being stained with FITC-labeled anti-CD3 and PE-labeled anti-IgG4 antibodies. The cells were washed and fixed before analysis by flow cytometry. The number of CD3+/IgG4+ cells was determined for each parameter and the percentage of occupancy for the exemplary anti-PD-1 antibody was determined as follows:

[Number of CD3+/IgG4+ cells for IgG4 treated cells at a given pre-incubation concentration of anti-PD-1 antibody] divided by

[Number of CD3+/IgG4+ cells for exemplary anti-PD-1 antibody treated cells at a given pre-incubation concentration of anti-PD-1 antibody]

For PBMCs pre-incubated with exemplary anti-PD-1 antibody, both the IgG4 treated as well as anti-PD-1 antibody treated cells generated a high number of CD3+/IgG4+ cells. As the level of exemplary anti-PD-1 antibody was reduced during the pre-incubation step, the number of CD3+/IgG4+ cells detected with the IgG4 treated cells steadily decreased, indicative of concentration dependent occupancy of PD-1 by exemplary anti-PD-1 antibody (FIG. 1).

This example demonstrates that anti-PD-1 antibodies within the scope of the present invention can bind natively expressed PD-1 and further that the occupancy of PD-1 on PBMCs by exemplary anti-PD-1 antibody is concentration dependent.

EXAMPLE 4

An Exemplary Anti-PD-1 Antibody Blocks Interaction Between PD-1 and PD-L1 and PD-L2

This example describes the ability of an exemplary anti-PD-1 antibody (having heavy and light chains as set forth in SEQ ID NOs: 1 & 2, respectively) to prevent the interaction between PD-1 and its cognate ligands, PD-L1 and PD-L2.

In these studies, human PD-L1 and PD-L2 mouse IgG1 Fc fusion proteins were expressed, purified, and labeled with DyL650. The dose-response of binding of both PD-L1 and PD-L2 to PD-1 CHO-K1 cells was determined. To quantify blocking of ligand binding to PD-1 CHO-K1 cells, exemplary anti-PD-1 antibody or IgG4 control antibody in a 3-fold dilution series was pre-mixed with PD-L1-mFc-DyL650 or PD-L2-mFc-DyL650. The mixture was added to human PD-1 CHO-K1 cells (3E5 cells) and incubated at 4° C. Cells were washed once and re-suspended in the presence of propidium iodide and DyL650-PD-L1 or DyL650-PD-L2. Binding was analyzed on a BD FACSArray (BD Bioscience), excluding dead cells. Data were analyzed for median fluorescence intensity and curves were fitted for $IC_{50}$ calculation using non-linear regression analysis in GraphPad Prism (Graphpad Software, Inc.) It was found that, unlike an IgG4 control antibody, an exemplary anti-PD-1 antibody (having heavy and light chains as set forth in SEQ ID NOs: 1 & 2, respectively) was able to potently inhibit the interaction between PD-1 and both PD-L1 and PD-L2 (Table 5).

TABLE 5

Potency of an exemplary anti-PD-1 antibody to inhibit the interaction between cell-expressed PD-1 and soluble PD-L1 and PD-L2

| Antibody | PD-L1/PD-1 CHO-K1 competition $IC_{50}$ (nM) | PD-L2/PD-1 CHO-K1 competition $IC_{50}$ (nM) |
|---|---|---|
| Exemplary anti-PD-1 antibody (having heavy and light chains as set forth in SEQ ID NOs: 1 & 2, respectively) | 1.8 | 1.5 |

This example demonstrates that anti-PD-1 antibodies within the scope of the present invention can block the binding of PD-1 ligands such as PD-L1 and PD-L2.

Having thus described at least several aspects and embodiments of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description are by way of example only and the invention is described in detail by the claims that follow.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. An antibody that binds programmed cell death 1 (PD-1) comprising: a heavy chain polypeptide comprising the amino acid sequence of SEQ ID NO: 1; and a light chain polypeptide comprising the amino acid sequence of SEQ ID NO: 2.

2. A composition comprising the antibody of claim 1 and a pharmaceutically acceptable carrier.

3. A method of treating a cancer or infection in a human that is responsive to PD-1 inhibition, which method comprises administering to the human an effective amount of the antibody of claim 1, whereupon the cancer or infection is treated in the human.

4. The method of claim 3, wherein the disorder is cancer.

5. The method of claim 4, wherein the cancer is selected from the group consisting of endometrial cancer, breast cancer, ovarian cancer, cervical cancer, and lung cancer.

6. The method of claim 3, wherein the method further comprises administering to the human has an agent that inhibits T cell immunoglobulin and mucin domain 3 (TIM 3).

7. The method of claim 3, wherein the method further comprises administering to the human an agent that inhibits lymphocyte-activation gene 3 (LAG-3).

8. The method of claim 3, wherein the method further comprises administering to the human an agent that inhibits poly (ADP-ribose) polymerase (PARD).

9. A method of manufacturing the antibody of claim 1, the method comprising expressing a nucleic acid encoding the antibody agent in a host cell culture.

10. An isolated nucleic acid sequence encoding a polypeptide comprising the amino acid sequence of SEQ ID NO: 1 or SEQ ID NO: 2.

11. A vector comprising the isolated nucleic acid of claim 10.

12. An isolated cell comprising a vector of claim 11.

13. The isolated nucleic acid sequence of claim 10, wherein the nucleic acid sequence encodes a polypeptide consisting of the amino acid sequence of SEQ ID NO: 1 and encodes a polypeptide consisting of the amino acid sequence of SEQ ID NO: 2.

14. An isolated nucleic acid comprising the nucleic acid sequence of SEQ ID NO:3 or SEQ ID NO:4.

* * * * *

UNITED STATES PATENT AND TRADEMARK OFFICE
CERTIFICATE OF CORRECTION

PATENT NO. : 11,155,624 B2
APPLICATION NO. : 16/346485
DATED : October 26, 2021
INVENTOR(S) : David J. King, Marilyn Kehry and Baochuan Huang Page 1 of 1

It is certified that error appears in the above-identified patent and that said Letters Patent is hereby corrected as shown below:

In the Claims

In Column 43, Line 43 (Claim 6), after "human" delete "has".

In Column 44, Line 29 (Claim 8), delete "(PARD)." And insert -- (PARP). --, therefor.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 6

<210> SEQ ID NO 1
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
```

```
            210                 215                 220
Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Leu His Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
        165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gaggtgcagc tgttggagtc tgggggaggc ttggtacagc ctggggggtc cctgagactc        60
tcctgtgcag cctctggatt cactttcagt agctatgaca tgtcttgggt ccgccaggct       120
ccagggaagg gctggagtg gtctcaacc attagtggtg gtggtagtta cacctactat        180
caagacagtg tgaaggggcg gttcaccatc tccagagaca attccaagaa cacgctgtat       240
ctgcaaatga acagcctgag agccgaggac acggccgtat attactgtgc gtccccttac       300
tatgctatgg actactgggg gcaagggacc acggtcaccg tctcctcagc atccaccaag       360
ggcccatcgg tcttccccgct agcaccctgc tccaggagca cctccgagag cacagccgcc       420
ctgggctgcc tggtcaagga ctacttcccc gaaccagtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cgaagaccta cacctgcaac       600
gtagatcaca agcccagcaa caccaaggtg gacaagagag ttgagtccaa atatggtccc       660
ccatgcccac catgcccagc acctgagttc ctgggggac catcagtctt cctgttcccc       720
ccaaaaccca aggacactct catgatctcc cggacccctg aggtcacgtg cgtggtggtg       780
gacgtgagcc aggaagaccc cgaggtccag ttcaactggt acgtggatgg cgtggaggtg       840
cataatgcca agacaaagcc gcgggaggag cagttcaaca gcacgtaccg tgtggtcagc       900
gtcctcaccg tcctgcacca ggactggctg aacggcaagg agtacaagtg caaggtctcc       960
aacaaaggcc tcccgtcctc catcgagaaa accatctcca aagccaaagg gcagccccga      1020
gagccacagg tgtacaccct gcccccatcc caggaggaga tgaccaagaa ccaggtcagc      1080
ctgacctgcc tggtcaaagg cttctacccc agcgacatcg ccgtggagtg ggagagcaat      1140
gggcagccgg agaacaacta caagaccacg cctcccgtgc tggactccga cggctccttc      1200
ttcctctaca gcaggctaac cgtggacaag agcaggtggc aggaggggaa tgtcttctca      1260
tgctccgtga tgcatgaggc tctgcacaac cactacacac agaagagcct ctccctgtct      1320
ctgggtaaa                                                              1329
```

<210> SEQ ID NO 4
<211> LENGTH: 642
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 4

```
gacatccagt tgacccagtc tccatccttc ctgtctgcat atgtaggaga cagagtcacc      60
atcacttgca aggccagtca ggatgtgggt actgctgtag cctggtatca gcaaaaacca     120
gggaaagccc ctaagctcct gatctattgg catccaccc tgcacactgg ggtcccatca      180
aggttcagcg gcagtggatc tgggacagaa ttcactctca caatcagcag cctgcagcct     240
gaagattttg caacttatta ctgtcagcat tatagcagct atccgtggac gtttggccag     300
gggaccaagc tggagatcaa acggactgtg gctgcaccat ctgtcttcat cttcccgcca     360
tctgatgagc aattgaaatc tggaactgcc tctgttgtgt gcctgctgaa taacttctat     420
cccagagagg ccaaagtaca gtggaaggtg ataacgccc tccaatcggg taactcccag      480
gagagtgtca cagagcagga cagcaaggac agcacctaca gcctcagcag cacccctgacg    540
ctgagcaaag cagactacga gaaacacaaa gtctacgcct gcgaagtcac ccatcagggc     600
ctcagctcgc ccgtcacaaa gagcttcaac aggggagagt gt                        642
```

<210> SEQ ID NO 5
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Asp Met Ser Trp Val Arg Gln Ala Pro Gly Lys Gly Leu
        50                  55                  60

Glu Trp Val Ser Thr Ile Ser Gly Gly Gly Ser Tyr Thr Tyr Tyr Gln
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ser Pro Tyr Tyr Ala Met Asp Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205
```

```
Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460

<210> SEQ ID NO 6
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Tyr Val Gly Asp Arg Val Thr Ile Thr Cys Lys Ala Ser
        35                  40                  45

Gln Asp Val Gly Thr Ala Val Ala Trp Tyr Gln Gln Lys Pro Gly Lys
    50                  55                  60

Ala Pro Lys Leu Leu Ile Tyr Trp Ala Ser Thr Leu His Thr Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Gln His
            100                 105                 110
```

```
Tyr Ser Ser Tyr Pro Trp Thr Phe Gly Gln Gly Thr Lys Leu Glu Ile
        115             120                 125
Lys Arg Thr Val Ala Ala Pro Ser Val Phe Ile Phe Pro Pro Ser Asp
    130             135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
            165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```